(12) United States Patent
Mumm et al.

(10) Patent No.: US 8,431,768 B2
(45) Date of Patent: Apr. 30, 2013

(54) TARGETED AND REGIONAL CELLULAR ABLATION IN ZEBRAFISH

(75) Inventors: Jeffrey S. Mumm, St. Louis, MO (US); Eric H. Schroeter, Troy, IL (US)

(73) Assignee: Washington University, St. Louis, MO (US)

( * ) Notice: Subject to any disclaimer, the term of this patent is extended or adjusted under 35 U.S.C. 154(b) by 12 days.

(21) Appl. No.: 13/287,372

(22) Filed: Nov. 2, 2011

(65) Prior Publication Data
US 2012/0144505 A1 Jun. 7, 2012

Related U.S. Application Data

(62) Division of application No. 12/394,740, filed on Feb. 27, 2009, now Pat. No. 8,071,838, which is a division of application No. 10/799,372, filed on Mar. 12, 2004, now Pat. No. 7,514, 595.

(60) Provisional application No. 60/454,486, filed on Mar. 13, 2003.

(51) Int. Cl.
*A01K 67/027* (2006.01)
*G01N 33/00* (2006.01)
*A01N 43/04* (2006.01)
*A61K 31/70* (2006.01)

(52) U.S. Cl.
USPC .................. 800/3; 514/44; 435/375; 800/20

(58) Field of Classification Search ...................... 800/20
See application file for complete search history.

(56) References Cited

U.S. PATENT DOCUMENTS 5,633,158 A 5/1997 Anlezark et al.

OTHER PUBLICATIONS

Naciff et al., "Identification and transgenic analysis of a murine promoter that targets cholinergic neuron expression", Journal of Neurochemistry, 1999, 72, pp. 17-28.
Naruse et al., "A detailed linkage map of medaka, *Oryzias latipes*: comparative genomics and genome evolution", Genetics, 2000, 154, pp. 1773-1784.
Nasevicius et al., "Effective targeted gene 'knockdown' in zebrafish", Nature Genetics, 2000, 26 pp. 216-220.
Ozato et al., "Production of transgenic fish: introduction and expression of chicken delta-crystallin gene in medaka embryos", Cell Differ Dev., 1986, 19, pp. 237-244.
Ozato et al., "Medaka as a model of transgenic fish", 1992, Mol Mar Biol Biotechnol, 1, pp. 346-354.
Park et al., "Analysis of upstream elements in the HuC promoter leads to the establishment of transgenic zebrafish with fluorescent neurons", Developmental Biology, 2000, 227, pp. 279-293.
Patton et al., "The art and design of genetic screens: zebrafish", Nature Reviews Genetics. 2001, 2, pp. 956-966.
Peterson et al., "Small molecule developmental screens reveal the logic and timing of vertebrate development", Proceedings of the National Academy of Sciences of the United States of America, 2000, 97, pp. 12965-12969.
Pinilla et al., "Advances in the use of synthetic combinatorial chemistry: Mixture-based libraries", Nature Medicine, 2003, 9, pp. 118-122.
Poss et al., "Tales of regeneration in zebrafish", Development Dynamics, 2003, 226, pp. 202-210.
Poss et al., "Heart regeneration in zebrafish", Science, 2002, 298, pp. 2188-2190.
Rawls et al., "Coupled mutagenesis screen and genetic mapping in zebrafish", Genetics in press, 2003.
Reimschussel, "A fish model of renal regeneration and development" Ilar Journal, 2001, 42, pp. 285-291.
Rowlerson et al., "Regeneration of skeletal muscle in two teleost fish: *Sparus aurata* and *Brachydanio rerio*", Cell & Tissue Research, 1997, 289, pp. 311-322.
Sato et al., "Firefly luciferase gene transmission and expression in transgenic medaka (*Oryzias latipes*)", Mol Mar Bid Biotechnol, 1992, 1, pp. 318-325.
Scheer et al. "Use of the Ga14-UAS technique for targeted gene expression in the zebrafish", Mechanisms of Development, 1999, 80, pp. 153-158.
Shinotoh et al., "Progressive loss of cortical acetylcholinesterase activity in association with cognitive decline in Alzheimer's disease: a positron emission tomography study", Annals of Neurology, 2000, 48, pp. 194-200.
Solnica-Krezel et al., "Efficient recovery of ENU-induced mutations from the zebrafish germline", Genetics, 1994 136, pp. 1401-1420.
Streisinger et al., "Production of clones of homozygous diploid zebra fish (*Brachydanio rerio*)", Nature, 1981, 291, pp. 293-296.
Sunderland, "Alzheimers disease. Cholinergic therapy and beyond", American Journal of Geriatric Psychiatry, 1998, 6, S56-S63.
Talbot et al., "Positional cloning of mutated zebrafish genes", Methods in Cell Biology, 1999, 60, pp. 259-286.
Tsien, "Rosy dawn for fluorescent proteins", Nature Biotechnology, 1999, 17, 956-957.

(Continued)

*Primary Examiner* — Valarie Bertoglio
(74) *Attorney, Agent, or Firm* — Armstrong Teasdale LLP

(57) ABSTRACT

A system including: (i) a methodology for targeted cellular ablation in zebrafish; (ii) a methodology for regional cellular ablation in zebrafish. These methodologies are used to identify drug compounds that influence cellular regeneration for the purpose of developing therapies for degenerative conditions. Transgenic zebrafish disclosed herein contain transgenic constructs composed of: (i) cell and/or tissue-type specific regulatory elements (e.g. promoter and/or enhancer regions) which delimit expression of operably linked gene product(s) to discrete cellular populations; (ii) a gene product that promotes cellular ablation composed of a pro-drug conversion system capable of converting nontoxic pro-drugs into cytotoxic drugs, which is expressed alone or in connection with; (iii) a reporter gene product that allows selective detection of cells expressing the reporter—both prior to (initial cells) and following cellular ablation (regenerated cells).

19 Claims, 5 Drawing Sheets

OTHER PUBLICATIONS

Tsien et al., "Seeing the machinery of live cells", Science, 1998, 280, pp. 1954-1955.
Vihtelic et al. "Light-induced rod and cone cell death and regeneration the in adult albino zebrafish (*Danio rerio*) retina", Journal of Neurobiology, 2000, 44, pp. 289-307.
Wang et al., "Use of an IRES bicistronic construct to trace expression of exogenously introduced mRNA in zebrafish embryos", Biotechniques, 2000, 29.
Wilson et al., "Quantitation of bystander effects in nitroreductase suicide gene therapy using three-dimensional cell cultures," Cancer Research, 2002, 62, pp. 1425-1432.
Xu et al., "Strategies for enzyme/prodrug cancer therapy", Clinical Cancer Research, 2001, 7, pp. 3314-3324.
Zhang et al., "Creating new fluorescent probes for cell biology", Nature Reviews Molecular Cell Biology, 2002, 3, pp. 906-912.
Zupanc, "Adult neurogenesis and neuronal regeneration in the central nervous system of teleost fish", Brain, Behavior & Evolution, 2001, 58, pp. 250-275.
Udvadia et al., "Windows into development: historic, current and future perspectives on transgenic zebrafish", Dev. Biol., 2003, 256, pp. 1-17.
Udvadia et al.,"GAP-43 promoter elements in transgenic zebrafish reveal a difference in signals for axon growth during CNS development and regeneration", Development, 2001, 128, pp. 1175-1182.
Ju et al., "Faithful expressionof green fluorescent protein (GFP) in transgenic zebrafish embryos under control of zebrafish promoters", Developmental Genetics, 1999, 25, pp. 158-167.
Higashijima, "High-frequency generation of transgenic zebrafish which reliably express GFP in whole muscles or the whole body using promoters of zebrafish origin" Dev. Biol., 1997, 192, pp. 289-299.
Huang et al, "Germ-line transmission of a myocardium specific GFP transgene reveals critical regulatory elements in the cardiac myosin light chain 2 promoter of zebrafish", Dev Dynam, 2003, 228, pp. 30-40.
Godinho et al., "Targeting of amacrine cell neurites to appropriate synaptic laminae in the developing zebrafish retina" Research Article Development, 2005, 132, pp. 5069-5079.
Perkins et al., "Transgenic expression of a GFP-rhodopsin COOH-terminal fusion protein in zebrafish rod photoreceptors", Visual Neuroscience, 2002, 19, pp. 257-264.
Reinhard et al., "Neural selective activation and temporal regulation of a mammalian GAP-43 promoter in zebrafish", Development, 1994, 120, pp. 1767-1775.
Rothenberg, "Mapping of complex regulatory elements by pufferfish/zebrafish transgenesis", PNAS, 2001, 98, 12, pp. 6540-6542.
Kay et al., "Transient requirement for ganglion cells during assembly of retinal synaptic layers", Research Article Development, 2004, 131, pp. 1331-1342.
Isles et al., "Conditional ablation of neurones in transgenic mice" J Neurobiol, 2001, 47, pp. 183-193.
Amsterdam et al., "A large-scale insertional mutagenesis screen in zebrafish", Genes & Development, 1999, 13, pp. 2713-2724.
Babic, "The cholinergic hypothesis of Alzheimer's disease: a review of progress", Journal of Neurology, Neurosurgery & Psychiatry, 1999, 67, p. 558.
Bagshawe et al., "Developments with targeted enzymes in cancer therapy", Current Opinion in Immunology, 1999, 11, pp. 579-583.
Beattie et al., "Early pressure screens", Methods in Cell Biology, 1999, 60, pp. 71-86.
Becker et al., "Axonal regrowth after spinal cord transection in adult zebrafish", Journal of Comparative Neurology, 1997, 377, pp. 577-595.
Bridgewater et al., "The bystander effect of the nitroreductase/CB 1954 enzyme/prodrug system is due to a cell-permeable metabolite", Human Gene Therapy, 1997, 8, pp. 709-717.
Brockerhoff et al., "A behavioral screen for isolating zebrafish mutants with visual system defects", Proc Nail Acad Sci U S A, 1995, 92, pp. 10545-10549.
Burkhardt-Holm et al., "Toxicity of 4-ehloroaniline in early life stages of zebrafish (*Danio rerio*): II. Cytopathology and regeneration of liver and gills after prolonged exposure to waterborne 4-chloroaniline", Archives of Environmental Contamination & Toxicology, 1999, 37, pp. 85-102.
Cameron et al., "Cell mosaic patterns in the native and regenerated inner retina of zebrafish: Implications for retinal assembly", Journal of Comparative Neurology, 2000, 416, pp. 356-367.
Chalfie, "Green fluorescent protein", Photochemistry & Photobiology, 1995, 62, 651-656.
Chalfie et al., "Green fluorescent protein as a marker for gene expression", Science, 1994, 263, 802-805.
Chou et al., "Uniform GFP-expression in transgenic medaka (*Oryzias latipes*) at the F0 generation", Transgenic Res., 2001, 10, pp. 303-315.
Denny, "Prodrug strategies in cancer therapy", European Journal of Medicinal Chemistry, 2001, 36, pp. 577-595.
Denny, "Nifroreductase-based GDEPT", Current Pharmaceutical Design, 2002, 8, pp. 1349-1361.
Driever et al., "A genetic screen for mutations affecting embryogenesis in zebrafish", Development 123, 1996, pp. 37-46.
Driever et al., "Zebrafish: genetic tools for studying vertebrate development", Trends in Genetics, 1994, 10, pp. 152-159.
Fareed et al., "Suicide gene transduction sensitizes murine embryonic and human mesenchymal stem cells to ablation on demand—a fail-safe protection against cellular misbehavior", Gene Therapy, 2002, 9, pp. 955-962.
Felmer et al., "Inducible ablation of adipocytes in adult transgenic mice expressing the *E-coli* nitroreductase gene", Journal of Endocrinology, 2002, 175, pp. 487-498.
Gong et al., "Green fluorescent protein (GFP) transgenic fish and their applications" Genetica, 2001, 111, pp. 213-225.
Grabher et al., "Transposon-mediated enhancer trapping in medaka", Gene, 2003, 322, pp. 57-66.
Gross et al., "The structure of the chromophore within DsRed, a red fluorescent protein front coral", Proceedings of the National Academy of Sciences of the United States of America, 2000, 97, pp. 11990-11995.
Grunwald et al., "Induction of recessive lethal and specific locus mutations in the zebrafish with ethyl nilrosourea", Genetical Research, 1992, 59, 103-1161.
Haffter et al., "The identification of genes with unique and essential functions in the development of the zebrafish, *Danio rerio*", Development, 1996, 123, pp. 1-36.
Hamaoka et al., "Visualization of rod photoreceptor development using GFP-transgenic zebrafish", Genesis, 2002, 34, pp. 215-220.
Heim et al., "Engineering green fluorescent protein for improved brightness, longer wavelengths and fluorescence resonance energy transfer", Current Biology, 1996, 6, pp. 178-182.
Henion et al., "Screen for Mutations Affecting Development of Zebrafish Neural Crest", Developmental Genetics, 1996, 18, pp. 11-17.
Houdebine et al., "Transgenesis in fish". Experientia, 1991, 47, pp. 891-897.
Hsiao et al., "Enhanced expression and stable transmission of transgenes flanked by inverted terminal repeats from adeno associated virus in zebrafish", Dev Dyn, 2001, 220, pp. 323-336.
Hulme et al., "Multi-component Reactions Emerging Chemistry in Drug Discovery' From Xylocain to Crixivan", Current Medicinal Chemistry, 2003, 10, pp. 51-80.
Ishikawa, "Medakafish as a model system for vertebrate developmental genetics", Bioessays, 2000, 22, pp. 487-495.
Ismail et al., "Nitroreductase—A New Live Cell Gene Reporter Assay System", Paper presented at: SBS 7th Annual Conference & Exhibition, 2001.
Ivics et al., "Genetic applications of transposons and other repetitive elements in zebrafish", Methods in Cell Biology, 60, 1999, pp. 99-131.
Kay et al., "Transient requirement for ganglion cells dining assembly of synaptic layer formation", Development, 2004, 131, pp. 1331-1342.

Kennedy et al., "Isolation of a zebrafish rod opsin promoter to generate a transgenic zebrafish line expressing enhanced green fluorescent protein in rod photoreceptors", Journal of Biological Chemistry, 2001, 276, pp. 14037-14043.

Knox et al., "The nitroreductase enzyme in Walker cells that activates 5-(aziridin-1-yl)-2,4-dinitrobenzamide (CB 1954) to 5-(aziridin-1-yl)-4-hydroxylaniino-2-nitrobenzamide is a form of NAD(P)H dehydrogenase (quinone) (EC 1.6.99.2)", Biochemical Pharmacology, 1988, 37, pp. 4671-4677.

Koster et al., "Tracing transgene expression in living zebrafish embryos", Developmental Biology, 2001, 233, pp. 329-346.

Langenau et al., "Myc-induced T cell leukemia in transgenic zebrafish", Science, 2003, 299, pp. 887-890.

Lanzky et al., "The toxic effect of the antibiotic metronidazole on aquatic organisms", Chemosphere, 1997, 35, pp. 2553-2561.

Lauren et al., "Cytotoxicity phase of diethylnitrosante-induced hepatic neoplasia in medaka." Cancer Res, 1990, 50, 17, pp. 5504-5514.

Long et al., "GATA-I expression pattern can be recapitulated in living transgenic zebrafish using GFP reporter gene", Development, 1997, 124, pp. 4105-4111.

Lu et al., "Pantropic retroviral vector integration, expression, and germline transmission in medaka (*Oryzias latipes*)", Mol Mar Biol Biotechnol, 1997, 6, pp. 289-295.

Mario-Geysen et al., "A guide to drug discovery: Combinatorial compound libraries for drug discovery: an ongoing challenge", Nature Reviews Drug Discovery, 2003, 2, pp. 222-230.

Matsumoto et al. "Expression and transmission of wild-type pigmentation in the skin of transgenic orange-colored variants of medaka (*Oryzias latipes*) bearing the gene for mouse tyrosinase", Pigment Cell Res, 1992, 5, pp. 322-327.

Medico et al., "A gene trap vector system for identifying transcriptionalty responsive genes", Nature Biotechnology, 2001, 19, pp. 579-582.

Meng et al., "Transgenesis, Methods in Cell Biology", 1999, 60, p. 13348.

Moss et al., "Green Fluorescent Protein Marks Skeletal Muscle in Murine Cell Lines and Zebrafish", Gene, 1996, 173, pp. 89-98.

Motoike et al., "Universal GFP reporter for the study of vascular development", Genesis, 2000, 28, pp. 75-81.

Muller et al., "Search for enhancers: teleost models in comparative genomic and transgenic analysis of cis regulatory elements", Bioessays, 2002, 24, pp. 564-572.

Mullins et al., "Large-scale mutagenesis in the zebrafish: in search of genes controlling development in a vertebrate", Current Biology, 1994, 4, pp. 189-202.

Mullins et al., "Mutational approaches to studying embryonic pattern formation in the zebrafish", Current Opinion in Genetics & Development, 1993, 3, pp. 648-654.

Figure 1 - Flow Chart
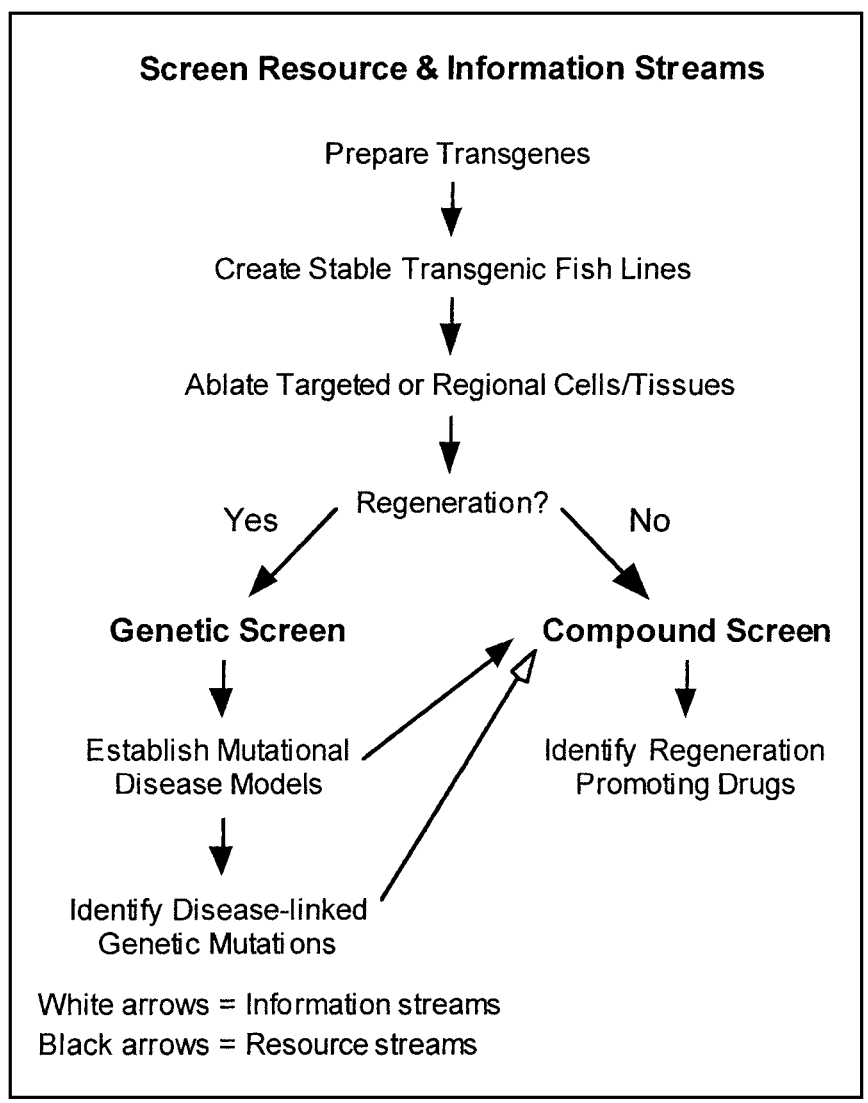

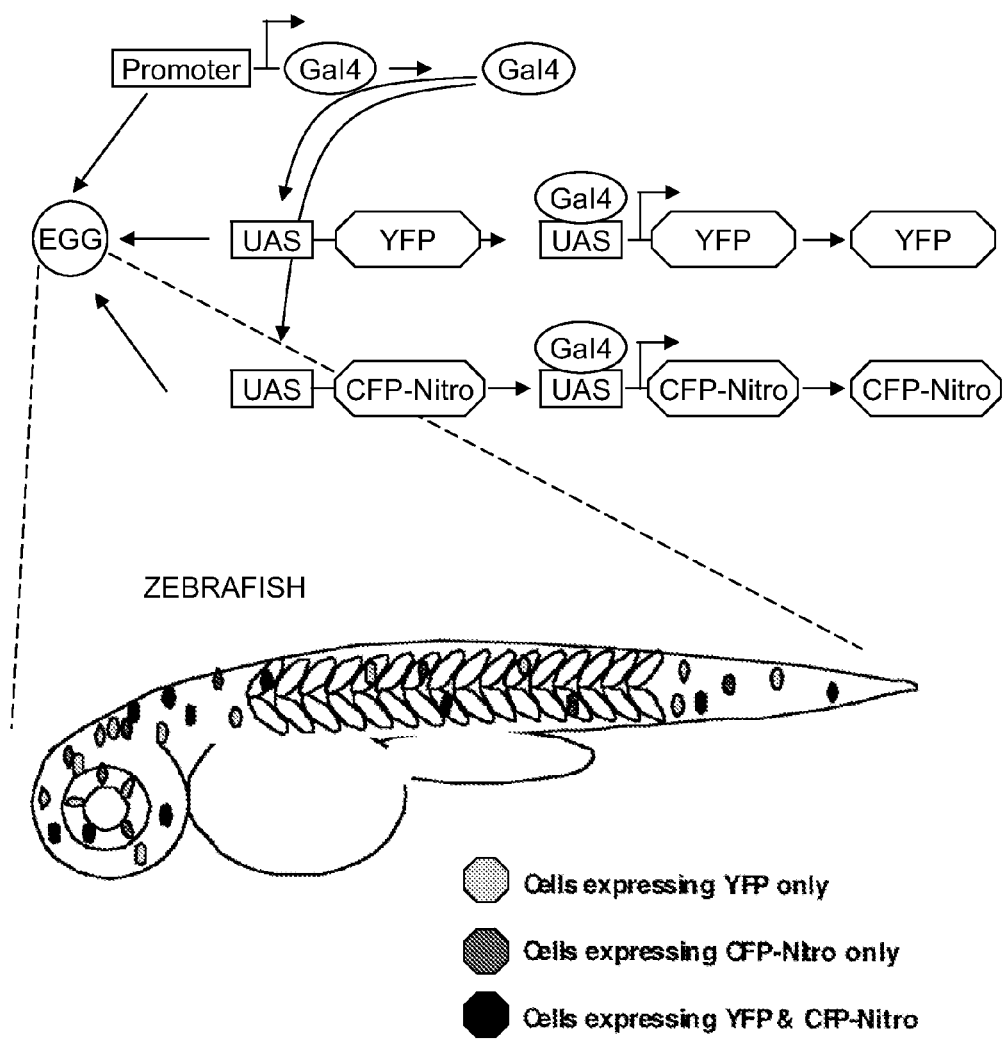
Figure 2 - Mosaic Expression System for Evaluating Ablation Methodology Figure 3 - Nitroreductase-mediated Targeted
Ablation Demonstrated In Transient Transgenic Zebrafish
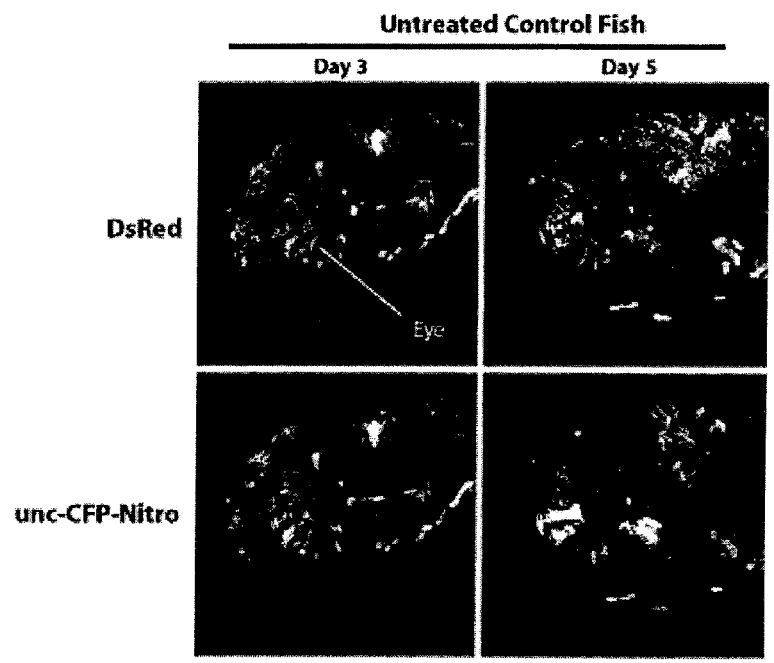
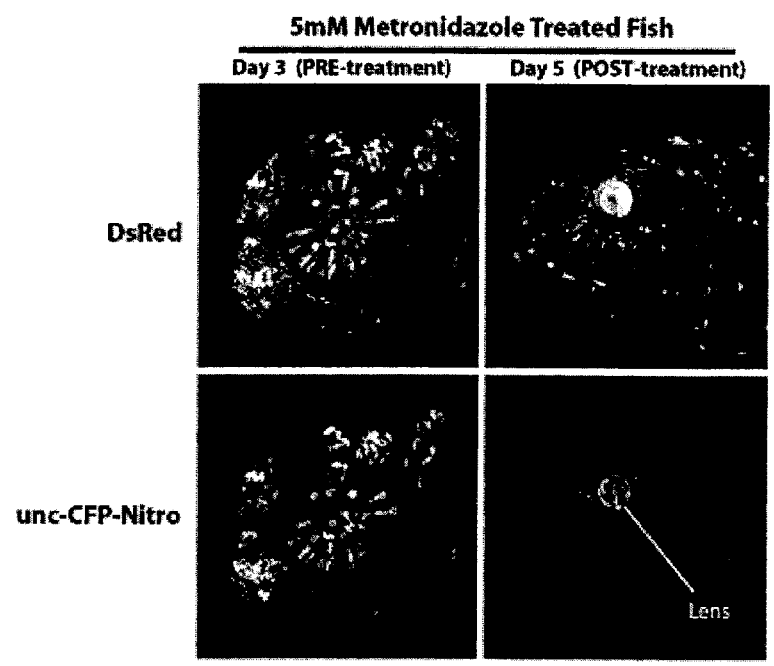

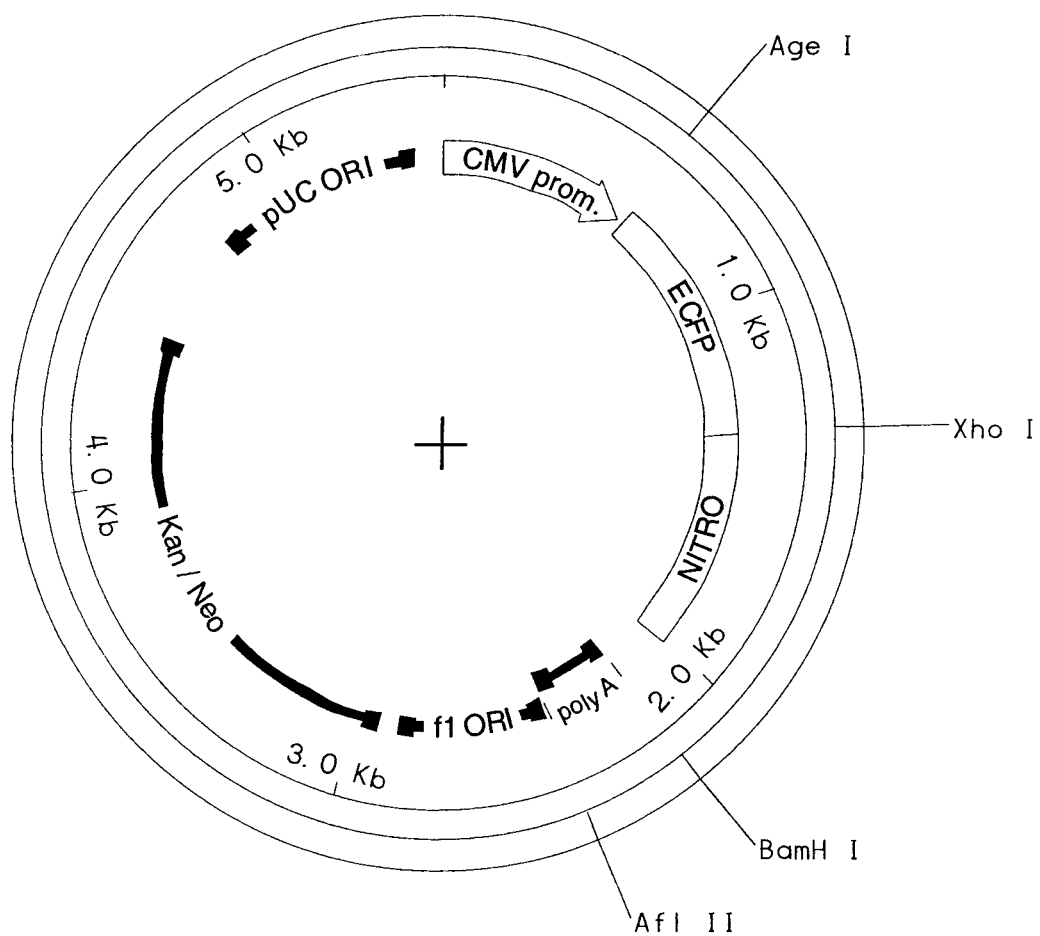
Figure 4 - pECFP-Nitroreductase Plasmid

Figure 5 - UAS::unc-CFP-Nitroreductase Plasmid
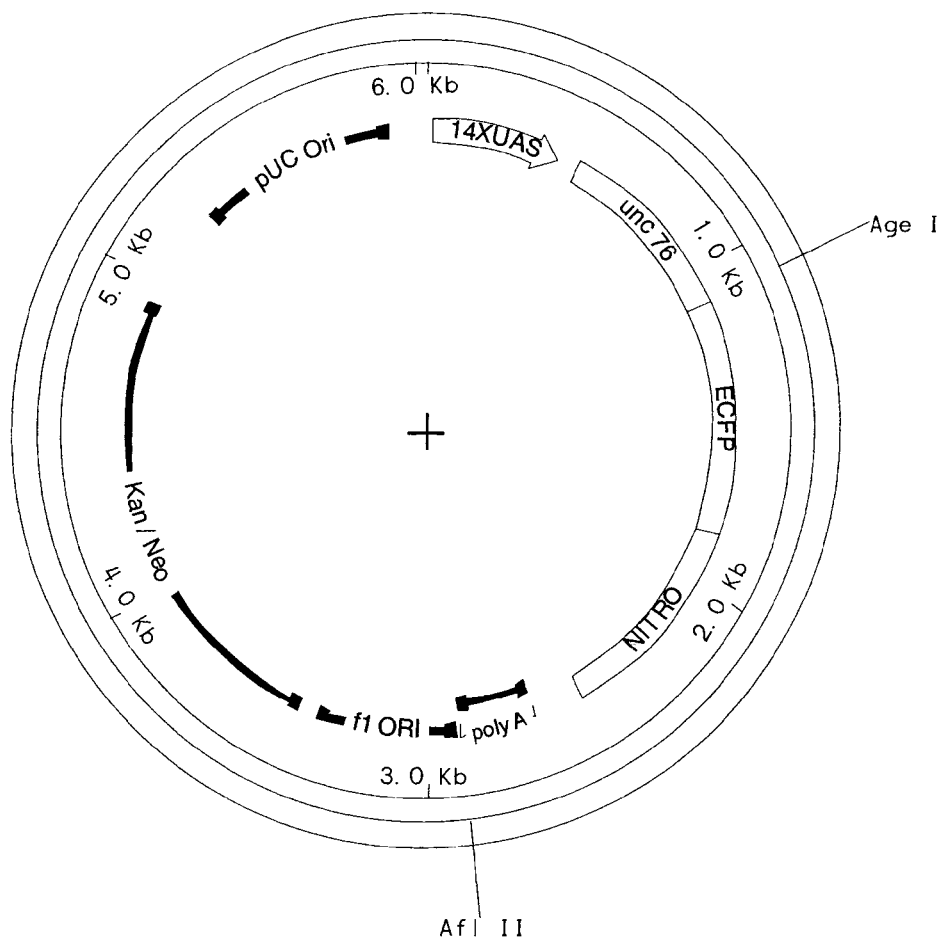

SEQUENCE LISTING

<160> NUMBER OF SEQ ID NOS: 3

<210> SEQ ID NO 1
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
atgctcgagc catggatatc atttctgtcg cctta                              35

<210> SEQ ID NO 2
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
ggggatccga tcgatctcaa tacccgctaa ata                                33

<210> SEQ ID NO 3
<211> LENGTH: 828
<212> TYPE: DNA
<213> ORGANISM: Escherichia coli

<400> SEQUENCE: 3
atgctcgagc catggatatc atttctgtcg ccttaaagcg tcattccact aaggcatttg    60
atgccagcaa aaacttacc ccggaacagg ccgagcagat caaaacgcta ctgcaataca   120
gcccatccag caccaactcc cagccgtggc attttattgt tgccagcacg gaagaaggta   180
aagcgcgtgt tgccaaatcc gctgccggta attacgtgtt caacgagcgt aaaatgcttg   240
atgcctcgca cgtcgtggtg ttctgtgcaa aaaccgcgat ggacgatgtc tggctgaagc   300
tggttgttga ccaggaagat gccgatggcc gctttgccac gccggaagcg aaagccgcga   360
acgataaagg tcgcaagttc ttcgctgata tgcaccgtaa agatctgcat gatgatgcag   420
agtggatggc aaaacaggtt tatctcaacg tcggtaactt cctgctcggc gtggcggctc   480
tgggtctgga cgcggtaccc atcgaaggtt ttgacgccgc catcctcgat gcagaatttg   540
gtctgaaaga gaaaggctac accagtctgg tggttgttcc ggtaggtcat cacagcgttg   600
aagattttaa cgctacgctg ccgaaatctc gtctgccgca aaacatcacc ttaaccgaag   660

-continued

```
tgtaattctc tcttgccggg catctgcccg gctatttcct ctcagattct cctgatttgc    720
ataaccctgt ttcagccgtc atcataggct gctgttgtat aaaggagacg ttatgcagga    780
tttaatatcc caggttgaag atttagcggg tattgagatc ggatcccc                 828
```

TARGETED AND REGIONAL CELLULAR ABLATION IN ZEBRAFISH

CROSS REFERENCE TO RELATED APPLICATIONS

This application claims priority to U.S. patent application Ser. No. 12/394,740, filed Feb. 27, 2009, now U.S. Pat. No. 8,071,838, which claims priority to U.S. patent application Ser. No. 10/799,372, filed Mar. 12, 2004, now U.S. Pat. No. 7,514,595, which claims priority to U.S. provisional patent application number 60/454,486, filed Mar. 13, 2003, all of which are incorporated herein in their entireties.

STATEMENT REGARDING FEDERALLY SPONSORED RESEARCH & DEVELOPMENT

This work was supported by grants front NIH including grants R01EY014358 and 1 F32EY14084-01. The government has certain rights in the invention.

FIELD OF THE INVENTION

This invention generally relates to novel transgenic zebrafish that serve as in vivo models for degenerative diseases and to their use for the identification of beneficial therapies and genetic programs that promote or influence cellular regeneration in vertebrates, including humans.

BACKGROUND OF THE INVENTION

Degenerative diseases are a major health issue of the twenty-first century, largely due to the global increase in the median age of humans. Recent findings suggest, however, that the human body retains a capacity for tissue specific stem cell activity even in regions formerly thought to be completely quiescent, such as the brain. Because the ability to induce and regulate cell type specific regeneration programs would represent the ultimate solution to degenerative diseases and conditions, a high-throughput vertebrate model system capable of fully elucidating the genetics and pharmacology of cellular regeneration is needed.

Zebrafish are an established model organism for investigating the genetics and pharmacology of vertebrate biology: Zebrafish are economical to maintain in the laboratory environment and are highly fecund; a single female is capable of generating hundreds of offspring per week. The zebrafish embryo develops externally and is transparent, allowing direct visualization of cellular and tissue developmental processes as they proceed in vivo, thereby facilitating large-scale genetic and small molecule drug screens. In the past several years numerous publications have reported transgenic fish lines expressing green fluorescent protein (GFP) in cell-type restricted expression patterns (Gong et al., 2001; Kennedy et al., 2001; Long et al., 1997; Moss et al., 1996; Motoike et al., 2000; Park et al., 2000). To date, studies using fluorescent transgenic zebrafish have focused mainly on imaging cells and tissues as they develop. Such transgenic zebrafish lines—in addition to promoting developmental investigations of tissue morphogenesis—facilitate genetic and pharmacological screens by allowing high-resolution imaging of discrete cell populations.

Moreover, as a disease model system, transgenic zebrafish provide a unique opportunity to elucidate cellular regeneration at the level of the entire genome of a vertebrate organism. This is due to a confluence of the required factors in this organism: 1) A robust capacity for cellular regeneration in a vertebrate; 2) Amenability to a forward genetics approach of random mutagenesis based screening; 3) Transparency, during embryonic, larval, and even into adult stages (given the proper genetic background) which allows the process of regeneration to be directly observed over time in the living organism, and; 4) Amenability to high-throughput genetic and pharmacological screening. Compared to other genetic models, zebrafish have the advantage of being more akin to humans than yeast, worms, or flies in terms of body plan (vertebrate) and genetic homology (75% and greater similarity to humans) and in being far more economical than nice. These are just a few of the reasons that zebrafish have emerged as the leading vertebrate model organism for large-scale 'forward genetics' based mutational screens (Driever et al., 1996; Haffter et al., 1996; Henion et al, 1996; Mullins et al., 1994). Furthermore, zebrafish have a remarkable regenerative capacity that extends even to their nervous system (Poss et al., 2003; Zupanc, 2001).

Pro-drug conversion systems have been reported by researchers as a method for targeted ablation of cancer cells (Denny, 2001). Several methods of delivering pro-drug converting systems specifically to cancer cells have been have been developed including, virus-directed enzyme pro-drug therapy (VDEPT), antibody-directed enzyme pro-drug therapy (ADEPT), and gene-directed enzyme pro-drug therapy (GDEPT). This system can also be applied to targeted and regional elimination ("ablation") of normal cells in order to study regeneration. Of particular interest are well studied pro-drug converting enzymes, such as bacterial nitroreductase, for which numerous pro-drugs with specific properties have been defined. For instance, certain pro-drugs can be used for targeted cell-specific ablation while other drugs promote more widespread regional ablation—whereby cells in the general vicinity of nitroreductase-expressing cells are also eliminated (Bridgewater et al., 1997). The regional ablation protocol, also called the 'bystander effect', can be used to model injury paradigms. In addition transgenic mice expressing prodrug conversion enzymes are able to specifically ablate cells in which the enzyme is expressed when these mice are treated with the appropriate prodrug (Felmer et al., 2002; Isles et al., 2001; Ma et al., 2002). Finally, a fusion protein between GFP and nitroreductase has been described which retains the function of both components in cell culture (Medico et al., 2001). Such fusion proteins ensure that the ablation component and reporter component do not segregate away from each other and allow definitive detection of all ablation competent expressing cells and regions.

Regenerative therapies are highly desired as an approach to curing degenerative conditions. Degenerative conditions include disorders such as Alzheimer's disease, Parkinson's disease, amyotrophic lateral sclerosis, spinal cord injury, traumatic brain injury, multiple sclerosis, cerebral palsy, osteoarthritis, and other age related forms of degeneration. Despite generally useful therapies including medicinal therapies currently available to ameliorate the symptoms of these afflictions, there is a substantial need for improved research tools to identify new compounds and to establish enhanced therapies for the treatment of these and other degenerative ailments.

Technical Problem: Ablation technology must fulfill several requirements in order to take advantage of the inherent regenerative capacity of the zebrafish and suitability to high-throughput analysis for finding both genes and compounds useful for the treatment of degenerative disorders These requirements include: 1) cell or tissue type specificity, 2) temporal control of ablation 3) adaptability to large scale high throughput analysis, and 4) ease of detection of both ablation and regeneration. A combination of all of these requirements is not available in current technology.

BRIEF DESCRIPTION OF THE INVENTION

Technical Solution: The invention described here fulfills previously unmet requirements by utilizing genetic delivery of an enzyme pro-drug system to ablate cells in fish selected from the group consisting of zebrafish and medaka. This universally applicable system has high specificity and temporal control with simple administration of a water soluble compound. In an aspect, this system is directly coupled with detection of the ablated and regenerating cells. This system enables the genetic dissection of the process of regeneration and high-throughput compound screening for the identification of drugs capable of promoting cellular and/or cell type specific regeneration in a vertebrate organism. Such drugs can then be applied to the problem of cellular regeneration and/or cell type specific regeneration in "higher" vertebrate model systems. The final aim being to identify drugs that can be introduced into clinical trials of degenerative disease/conditions, whereby the drug promotes cellular regeneration and/or cell type specific regeneration in humans in order to provide a cure for these debilitating disorders (see FIG. 1 for a flow chart of the invention).

In an aspect, fully characterized transgenic fish selected from the group consisting of zebrafish and medaka are derived from a transgenic construct (or, "transgene") comprising transgenic DNA sequences which capably and competently regulate the expression of and encode a transgenic gene product, the transgenic gene product comprising at least one of an ablation-promoting moiety or a coupled expression system of an ablation-promoting moiety and a reporter moiety, the ablation-promoting moiety comprising at least one component of a pro-drug conversion system, and the reporter moiety allowing selective detection of cells expressing the reporter moiety. As used herein, the terms "transgenic construct" or "transgene" or "transgenic DNA sequence", art used interchangeably and refer to the "transgenic DNA sequence" in the specification and claims.

In an aspect, the transgenic construct comprises regulatory DNA sequence operably linked to a sequence encoding a gene product(s) such that the regulatory sequence promotes specific expression of the gene product(s) in at least one of a specific cell, cell type(s), and/or tissue(s).

In an aspect, a method of making novel transgenic fish selected from the group consisting of zebrafish and medaka comprises introducing a transgenic construct into a fish egg cell or embryonic cell, wherein the transgenic construct comprises transgenic DNA sequences which capably and competently regulate the expression of and encode a gene product, the gene product comprising at least one of an ablation-promoting moiety or a coupled expression system of an ablation-promoting moiety and a reporter moiety, the ablation-promoting moiety comprising at least one component of a pro-drug conversion system and the reporter moiety allowing selective detection of cells expressing the reporter moiety. In an aspect associated therewith the transgenic construct is expressed only transiently during the development of the injected fish. In another aspect, the transgenic construct is heritable by virtue of its stable integration into the genome of the injected cell such that the cell develops into a potential "founder" transgenic fish capable of germline propagation of the transgene, whereby a reproducible expression pattern of the gene product is transmitted to the those progeny of the founder to which the transgene is transmitted.

In an aspect, the transgenic construct used to create novel transgenic fish selected from the group consisting of zebrafish and medaka comprises a regulatory DNA sequence operably linked to a sequence encoding the gene product such that the regulatory sequence promotes specific expression of the gene product in at least one of a specific cell, cell type(s), and/or tissue(s).

In an aspect, a targeted ablation and subsequent regeneration screening method for determining the inherent regenerative capacity of fish selected from the group consisting of zebrafish and medaka with respect to specific cells and/or tissue types is provided; novel transgenic fish—containing a transgenic construct comprised of transgenic DNA sequences which capably and competently regulate the expression of and encode a gene product, the gene product comprising at least one of an ablation-promoting moiety or a coupled expression system of an ablation-promoting moiety and a reporter moiety, the ablation-promoting moiety comprising at least one component of a pro-drug conversion system, and the reporter moiety allowing selective detection of cells expressing the reporter moiety—are exposed to an ablation-promoting pro-drug whereby at least one cell of the transgenic fish expressing a pro-drug converting moiety is brought into contact with the pro-drug and wherein the pro-drug is converted into a cytotoxic drug by action of the pro-drug converting moiety and whereby only those cells expressing the pro-drug converting moiety are ablated by action of the drug. Subsequent regeneration, or lack of regeneration, of the ablated cell(s) is detected by the general presence, or absence, of regenerating cells and/or the presence, or absence, of a cellular reporter expressed by regenerating cells.

In an aspect, a fish selected from the group consisting of zebrafish and medaka is determined to have an inherent capacity for regeneration of the ablated cell(s) and/or tissue(s) as determined by; screening novel transgenic fish—containing a transgenic construct comprised of transgenic DNA sequences which capably and competently regulate the expression of and encode a gene product, the gene product being comprised of at least one of an ablation-promoting moiety or a coupled expression system of an ablation-promoting moiety and a reporter moiety, the ablation-promoting moiety comprising at least one component of a pro-drug conversion system, and the reporter moiety allowing selective detection of cells expressing the reporter moiety—for the ability to regenerate ablated cells. The regeneration screen comprising a procedure whereby at least one cell of the transgenic fish expressing a pro-drug converting moiety is brought into contact with a pro-drug, and wherein the pro-drug is converted into a cytotoxic drug by action of the pro-drug converting moiety, and whereby only those cells expressing the pro-drug converting moiety are ablated by action of the drug. Subsequent regeneration of the ablated cell(s) is detected by the general presence of regenerating cells and/or the presence of a cellular reporter expressed by regenerating cells. Upon observation of regeneration the fish is determined to be regeneration-competent with respect to the specific cells and/or tissue types ablated.

In an aspect, a fish selected from the group consisting of zebrafish and medaka is determined to have no inherent capacity for regeneration of the ablated cell(s) and/or tissue(s) as determined by; screening novel transgenic fish—containing a transgenic construct comprised of transgenic DNA sequences which capably and competently regulate the expression of and encode a gene product, the gene product being comprised of at least one of an ablation-promoting moiety or a coupled expression system of an ablation-promoting moiety and a reporter moiety, the ablation-promoting moiety comprising at least one component of a pro-drug conversion system, and the reporter moiety allowing selective detection of cells expressing the reporter moiety—for the ability to regenerate ablated cells. The regeneration screen comprising a procedure whereby at least one cell of the transgenic fish expressing a pro-drug converting moiety is brought into contact with a pro-drug, and wherein the pro-drug is converted into a cytotoxic drug by action of the pro-drug converting moiety, and whereby only those cells expressing the pro-drug converting moiety are ablated by action of the drug. Subsequent lack of regeneration of the ablated cell(s) is detected by the general absence of regenerating cells and/or the absence of a cellular reporter expressed by regenerating cells. Upon finding no evidence of regeneration the fish is determined to be regeneration-deficient with respect to the specific cells and/or tissue types ablated.

In an aspect, the transgenic construct used to create novel transgenic fish selected from the group consisting of zebrafish and medaka that are utilized for determining the inherent regenerative capacity of the fish with respect to specific cell and/or tissue types comprises regulatory DNA sequence operably linked to a sequence encoding the gene product such that the regulatory sequence promotes specific expression of the gene product in at least one of a specific cell, cell type(s), and/or tissue(s).

In an aspect, a regional ablation and subsequent regeneration screening method for determining the inherent regenerative capacity of fish selected from the group consisting of zebrafish and medaka with respect to a modeled injury is provided; novel transgenic fish—containing a transgenic construct comprised of transgenic DNA sequences which capably and competently regulate the expression of and encode a gene product, the gene product being further comprised of at least one of an ablation-promoting moiety or a coupled expression system of an ablation-promoting moiety and a reporter moiety, the ablation-promoting moiety comprising at least one component of a pro-drug conversion system, and the reporter moiety allowing selective detection of cells expressing the reporter moiety—are exposed to an ablation-promoting pro-drug whereby at least one cell of the transgenic fish expressing a pro-drug converting moiety is brought into contact with a pro-drug, and wherein the pro-drug is converted into a cytotoxic drug by action of the pro-drug converting moiety and whereby the cell producing the cytotoxic drug as well as cells in the general vicinity of the cytotoxic drug producing cell are ablated by action of the drug. Subsequent regeneration, or lack of regeneration correspondingly, of the ablated cell(s) is detected by the general presence, or absence, of regenerating cells and/or the presence, or absence correspondingly, of a cellular reporter expressed by regenerating cells.

In an aspect, the fish selected from the group consisting of zebrafish and medaka is determined to have an inherent capacity for regeneration following a modeled injury as determined by; screening novel transgenic fish—containing a transgenic construct comprised of transgenic DNA sequences which capably and competently regulate the expression of and encode a gene product, the gene product being comprised of at least one of an ablation-promoting moiety or a coupled expression system of an ablation-promoting moiety and a reporter moiety, the ablation-promoting moiety comprising at least one component of a pro-drug conversion system, and the reporter moiety allowing selective detection of cells expressing the reporter moiety—for the ability to regenerate ablated cells following a modeled injury. The regeneration screen comprises a procedure whereby at least one cell of the transgenic fish expressing a pro-drug converting moiety is brought into contact with a pro-drug, and wherein the pro-drug is converted into a cytotoxic drug by action of the pro-drug converting moiety, and whereby the cell producing the cytotoxic drug as well as cells in the general vicinity of the cytotoxic drug producing cell are ablated by action of the drug. Subsequent regeneration of the ablated cell(s) is detected by the general presence of regenerating cells and/or the presence of a cellular reporter expressed by regenerating cells. Upon observation of regeneration the fish is determined to be regeneration-competent with respect to the ablated cells and/or tissue types (i.e. the modeled injury).

In an aspect, the fish selected from the group consisting of zebrafish and medaka is determined to have no inherent capacity for regeneration following a modeled injury as determined by; screening novel transgenic fish—containing a transgenic construct comprised of transgenic DNA sequences which capably and competently regulate the expression of and encode a gene product, the gene product being comprised of at least one of an ablation-promoting moiety or a coupled expression system of an ablation-promoting moiety and a reporter moiety, the ablation-promoting moiety comprising at least one component of a pro-drug conversion system, and the reporter moiety allowing selective detection of cells expressing the reporter moiety—for the ability to regenerate ablated cells following a modeled injury. The regeneration screen comprising a procedure whereby at least one cell of the transgenic fish expressing a pro-drug converting moiety is brought into contact with a pro-drug, and wherein the pro-drug is converted into a cytotoxic drug by action of the pro-drug converting moiety, and whereby the cell producing the cytotoxic drug as well as cells in the general vicinity of the cytotoxic drug producing cell are ablated by action of the drug. Subsequent lack of regeneration of the ablated cell(s) is detected by the general absence of regenerating cells and/or the absence of a cellular reporter expressed by regenerating cells. Upon finding no evidence of regeneration the fish is determined to be regeneration-deficient with respect to the cells and/or tissue types ablated (i.e. the modeled injury).

In an aspect, the transgenic construct used to create novel transgenic fish selected from the group consisting of zebrafish and medaka utilized for determining the inherent regenerative capacity of these fish with respect to a modeled injury comprises regulatory DNA sequence operably linked to a sequence encoding the gene product such that the regulatory sequence promotes specific expression of the gene product in at least one of a specific cell, cell type(s), and/or tissue(s).

In an aspect, a genetic screening method for identifying regeneration-deficient mutant fish is provided; regeneration-competent transgenic fish selected from the group consisting of zebrafish and medaka—having an inherent capacity for cellular regeneration with respect to specific cell and/or tissue types or with respect to a regional ablation—are subjected to targeted or regional cellular ablation within the context of a "forward genetics" mutagenesis screen. Mutant fish are identified which are compromised in terms of their regenerative capacity, whereby, the regeneration of ablated cell(s)—as detected by the general presence of regenerating cells and/or the presence of a cellular reporter expressed by regenerating cells—is reduced or absent in some percentage of embryos, larvae, or fish produced from a mutagenized germ cell (i.e. reduced or absent in mutant compared to wildtype siblings). Mutant fish with a compromised capacity for regeneration are determined to be regeneration-deficient with respect to specific cells and/or tissue types. In these instances regeneration-deficiency is due to a mutation(s) that causes an alteration in gene structure, gene product structure, gene product function, and/or gene product expression, thereby implicating the altered gene and/or gene product as a factor capable of influencing the process of cellular regeneration.

In an aspect, a genetic screening method for identifying regeneration-competent mutant fish is provided: regeneration-deficient transgenic fish selected from the group consisting of zebrafish and medaka—having an inherent incapacity for cellular regeneration with respect to specific cell and/or tissue types or with respect to a regional ablation—are subjected to targeted or regional cellular ablation within the context of a "forward genetics" mutagenesis screen. Mutant fish are identified which are have an enhanced regenerative capacity, whereby, the regeneration of ablated cell(s)—as detected by the general presence of regenerating cells and/or the presence of a cellular reporter expressed by regenerating cells—is increased in some percentage of embryos, larvae, or fish produced from a mutagenized germ cell (i.e. reduced or absent in mutant compared to wildtype siblings). Mutant fish with an enhanced capacity for regeneration are determined to be regeneration-competent with respect to specific cells and/or tissue types. In these instances regeneration-competency is due to a mutation(s) that causes an alteration in gene structure, gene product structure, gene product function, and/or gene product expression, thereby implicating the altered gene and/or gene product as a factor capable of influencing the process of cellular regeneration.

In an aspect, a method for identifying genes mutated in genetic screens comprises mapping a mutated gene to a discrete chromosomal region, subsequently narrowing down the identity of the mutated gene from a set of candidate genes in the chromosomal region, and cloning and sequencing the mutated gene to determine the precise site and nature of the mutation.

In an aspect, the transgenic construct used to create a novel regeneration-competent transgenic fish selected from the group consisting of zebrafish and medaka that are utilized in a genetic screening method for identifying mutant fish comprises regulatory DNA sequence operably linked to a sequence encoding the gene product such that the regulatory sequence promotes specific expression of the gene product in at least one of a specific cell, cell type(s), and/or tissue(s).

In an aspect, a pharmacological screening method for discovering drug compounds which promote cellular regeneration is provided. Regeneration-deficient transgenic fish selected from the group consisting of zebrafish and medaka having either an inherent incapacity for cellular regeneration or having been identified as mutants with a compromised capacity for cellular regeneration with respect to specific cell and/or tissue types, or with respect to a modeled injury, are subjected to targeted or regional cellular ablation within the context of a pharmacological screen. Compounds are tested for their ability to promote the regeneration of an ablated cell(s) or tissue type(s)—as detected by the general presence of regenerating cells and/or the presence of a cellular reporter expressed by regenerating cells—whereby transgenic fish maintained in the presence of a discrete molecular compound or sets of molecular compounds have an enhanced capacity for cellular regeneration, relative to transgenic fish maintained in control conditions. When a compound or set of compounds has been identified as capable of promoting an enhanced capacity for regeneration the compound(s) is deemed a target compound(s) capable of promoting the process of cellular regeneration.

In an aspect, a method for optimizing target compounds comprises obtaining chemical variants of target compounds through a combinatorial chemistry approach, or a company providing combinatorial chemistry services, the chemical variants being tested for properties such as, but not limited to, enhanced efficacy, enhanced solubility, and/or toxicity.

In an aspect, the transgenic construct used to create a novel regeneration-deficient transgenic fish selected from the group consisting of zebrafish and medaka utilized in a pharmacological screening method to identify drug compounds which promote cellular regeneration comprises regulatory DNA sequence operably linked to a sequence encoding the gene product such that the regulatory sequence promotes specific expression of the gene product in at least one of a specific cell, cell type(s), and/or tissue(s).

In an aspect, the transgenic construct comprises a minimal promoter element operably linked to an ablation promoting moiety or a co-expressed ablation-promoting moiety and reporter transgene product such that the transgenic construct can be randomly inserted and/or transposed in the genome of a fish selected from the group consisting of zebrafish and medaka using an "enhancer trap" strategy that facilitates random expression patterns that are dependent on properties of endogenous regulatory regions (e.g. enhancers and/or repressors) that act at the site of integration. For instance, enhancer trap lines can be created in fish using transposable elements (e.g. Sleeping Beauty, the Tcl/mariner-like family etc., Ivics et al., 1999) and fish that demonstrate expression patterns of interest can be propagated and utilized identically to other transgenic fish.

In an aspect, the transgenic construct comprises a heterologous gene product expression amplification system that is further comprised of regulatory DNA sequence operably linked to a heterologous DNA binding/activating gene product that, in turn, regulates expression of a transgene product(s) operably linked to activating sequences specific for the given binding protein. In particular, The Gal4-UAS system has been shown to be operative in fish (Koster and Fraser, 2001; Scheer and Campos-Ortega, 1999). Moreover, such systems can be structured as co-linear DNA molecules—whereby all elements are contained in a single DNA construct—or as modular units—whereby individual elements are contained in separate DNA constructs—that can be combined through co-introduction into a transgenic host and/or by deriving separate transgenic lines expressing individual modular units (or sets of modular units) that can be mated to produce offspring expressing combinations of the modular units contained in each parent.

In an aspect, the transgenic construct comprises an enhancer trap system comprising a minimal promoter element operably linked to a given DNA binding protein (e.g. Gal4-VP16 fusion) and a reporter gene product under regulation of corresponding activating sequences (e.g. UAS, upstream activating sequences specific for Gal4) such that the transgenic construct can be randomly inserted and/or transposed in the genome of fish using an "enhancer tap" strategy that facilitates random expression patterns that are dependent on properties of regulatory regions (e.g. enhancers and/or repressors) that act at the site of integration. For instance, enhancer trap Lines can be created in zebrafish using transposable elements (e.g. Sleeping Beauty, the Tcl/mariner-like family etc., Grabher et al., 2003; Ivics et al., 1999) and fish that demonstrate expression patterns of interest can be propagated and utilized identically to other transgenic fish.

In an aspect of this invention, regulatory DNA sequences which specify a desired expression pattern of operably linked gene products are derived from a fish from the group consisting of zebrafish and medaka (i.e. homologous to the transgenic fish) and recombined with the transgene product coding sequence in standard plasmid vectors using established cloning procedures, such as restriction enzyme digest and cohesive end ligation.

In an aspect, transgene product coding sequence is capably inserted into an endogenous gene product coding sequence of a fish selected from the group consisting of zebrafish and medaka genomic locus contained in an artificial chromosome system, the native gene product of which is expressed in a desired expression pattern, such that the transgene product can be expressed in the desired pattern, using established cloning procedures, such as bacterial recombination.

In an aspect, transgene product coding sequence is randomly inserted into the genome of a fish selected from the group consisting of zebrafish and medaka by virtue of the activity of a transposable element allowing native regulatory elements to be co-opted which regulate the spatial and temporal expression pattern of the gene product and desired expression patterns can be selected for, tested for germline transmission, and subsequently propagated as stable transgenic lines.

In an aspect, regulatory DNA sequences which specify a desired expression pattern of operably linked gene products are derived from a species different from that of the transgenic fish (i.e. heterologous) and recombined with the transgene product coding sequence in standard plasmid vectors using established cloning procedures, such as restriction enzyme digest and cohesive end ligation.

In an aspect, the transgene (product coding sequence) is inserted into the coding sequence of a heterologous (other than the transgenic fish) genomic locus contained in an artificial chromosome system, the gene product of which is expressed in the desired expression pattern, using established cloning procedures, such as bacterial recombination.

In an aspect, regulatory DNA sequences are derived from the pufferfish, "fugu" (Takjfugu rubripes).

BRIEF DESCRIPTION OF THE DRAWINGS

FIG. 1 depicts a flow chart detailing the sequence of events leading to, and during, and the interrelationship between genetic and compound screens of transgenic zebrafish of this invention.

FIG. 2 depicts a mosaic expression system for evaluating ablation based on Gal4/VP16-driver and UAS-reporter elements in transient transgenic zebrafish.

FIG. 3 depicts a demonstration of nitroreductase-mediated targeted ablation in the presence of the pro-drug metronidazole in transgenic zebrafish transiently expressing an unc-CFP-Nitroreductase fusion product and a DsRed control reporter.

FIG. 4 depicts a circular map of the pECFP-Nitroredustase plasmid.

FIG. 5 depicts a circular map of the UAS::unc-CFP-Nitroreductase plasmid.

A detailed description of the drawings is presented in the following text.

DETAILED DESCRIPTION OF THE INVENTION

In an aspect, the fish utilized to create transgenic fish disclosed herein is zebrafish (Danio). Further in that regard, it is seen from a reading of the description and claims of this application that all aspects of this invention which have been described as applying to zebrafish apply likewise to the fish, medaka (Ishikawa, 2001; Muller et al., 2002), in that technically (i.e. technical reality): 1) Medaka is amenable to transgenesis as described herein with respect to zebrafish (Ozato et al., 1986; Houdebine et al., 1991; Matsumoto et al, 1992; Ozato et al, 1992; Sato et al., 1992; Lu et al, 1997; Chou et al., 2001; Hsiao et al., 2001; Grabber et al., 2003); 2) Medaka is capable of cellular regeneration (Lauren et al., 1990); 3) The medaka genome is mapped (Naruse et al., 2000) and is currently being sequenced (Medaka Genome Initiative) and; 5) Medaka can be used in a manner substantially equivalently to zebrafish for high-throughput genetic and pharmacological screening procedures (Ishikawa, 2001; Muller et al., 2002) as described herein, with respect to zebrafish, such that genes, genetic mutations, and drugs, that impact the process of cellular regeneration in a vertebrate species are identified. Thus, in an aspect a transgenic fish comprising a transgenic medaka would be created and utilized in accordance with this invention in the same or substantially the same manner as the zebrafish aspects described herein (for non-limiting illustration only).

In an aspect, the fish utilized to create transgenic fish disclosed herein is medaka (Oryzias).

Disclosed herein are novel transgenic zebrafish that facilitate inducible targeted cellular ablation, a method of making such novel transgenic zebrafish and methodologies for using such novel transgenic zebrafish. More particularly, described here is a method for creating 'stable' transgenic fish lines which have stably integrated a pro-drug converting moiety into their genome such that the moiety is expressed in a reproducible pattern from generation to generation. Our discovery allows researchers to reveal the process of cellular regeneration at the level of entire genetic programs, both in terms of factors that serve as lowest common denominators for the regeneration of all cells and in terms of genes specific for the regeneration of defined cell types.

In an aspect, utilizing our discovery, forward saturation genetics are used to define genetic mutations that compromise the ability of zebrafish to regenerate specific cell types. Regeneration-deficient fish, in turn, represent models for degenerative conditions. Because zebrafish are eminently suited to high-throughput drug compound screening, degenerative zebrafish models facilitate the identification and optimization of drug compounds that promote cellular regeneration. Moreover, regeneration-promoting drug compounds represent bona fide cures for degenerative conditions.

The following descriptions, aspects, embodiments and preferred embodiments of our discovery are intended as illustrative examples only and in no aspect limiting the scope of our discovery.

Note that, unless clearly stated otherwise, for the purpose of clarity the singular forms of "a", "an", and "the" also refer to plural forms of the attending subject throughout this text.

The following definitions for terms used throughout this text are provided for the purpose of clarification and are not intended to be limiting on the scope of the invention.

As used herein, the term "zebrafish" refers to any fish or strain of fish that is considered to be of the genus and species, *Danio rerio*.

As used herein the term "transgenic" refers to an organism and the progeny of such an organism that contains a DNA molecule that has been artificially introduced into the organism.

As used herein, the terms "transgenic construct" or "transgene" or "transgenic DNA sequence", are used interchangeably and refer to a nucleic acid molecule typically comprised of, but not limited to, regulatory regions (e.g. promoter and enhancer sequences) that arc competent to initiate and otherwise regulate the expression of a gene product(s). Transgenic constructs may also contain any other mutually compatible DNA elements for controlling the expression and/or stability of the associated gene product(s), such as polyadenylation sequences. Transgenic constructs may also contain other DNA sequences which function to promote integration of operably linked DNA sequences into the genome of a zebrafish and any associated DNA elements contained in any nucleic acid system (e.g. plasmid expression vectors) used for the propagation, selection, manipulation and/or transfer of recombinant nucleic acid sequences. Moreover, transgenic constructs comprise transgenic DNA sequences encoding a gene product, the gene product comprising at least one of an ablation-promoting moiety or a coupled expression system of an ablation-promoting moiety and a reporter moiety, the ablation-promoting moiety comprising at least one component of a pro-drug conversion system, and the reporter moiety allowing selective detection of cells expressing the reporter moiety.

As used herein, the terms "regulatory DNA sequences" or "regulatory regions" or "DNA sequences which capably and competently regulate the expression of", are used interchangeably and refer to nucleic acid molecules which function as promoters, enhancers, insulators, silencers and/or other similarly defined DNA sequences which control the spatial and temporal expression of operably linked and/or associated gene products.

As used herein, the term "gene product" includes at least one of an ablation-promoting moiety or a coupled expression system of an ablation-promoting moiety and a reporter moiety, the ablation-promoting moiety comprising at least one component of a capable pro-drug conversion system, and the reporter moiety allowing selective detection of cells expressing the reporter moiety.

As used herein, the term "ablation-promoting moiety" includes at least one of a protein or RNA molecule. Useful ablation-promoting moieties include, but are not limited to, pro-drug converting enzymes such as bacterial nitroreductase (Denny, 2002).

As used herein, the term "reporter" includes a gene product that capably facilitates direct or indirect detection of the physical presence of a cell(s) and/or tissue(s) expressing the gene product. Useful reporters include, but are not limited to, fluorescent proteins (e.g. green fluorescent protein, (GFP), bioluminescence catalyzing enzymes (e.g. luciferase) and metabolic enzymes with colorimetric substrates (e.g. beta-galactosidase).

As used herein, the terms "coupled expression system" or co-expression system" refer to any method that allows two or more functional gene products to be co-regulated such that they are necessarily expressed in identical spatial and temporal patterns. Useful coupled expression systems include, but are not Limited to, protein-protein fusion(s), and internal ribosome entry sites (IRES).

As used herein, the term "pro-drug" includes a pharmacologically inert chemical derivative that can is converted to an active cytotoxic drug form. Useful pro-drugs include, but are not limited to those appropriate for pro-drug converting enzymes, such as CB 1954 and metronidazole (these being substrates for bacterial nitroreductase, Bridgewater et al., 1997).

As used herein, the term "pro-drug converting" or "pro-drug conversion" system includes one or more moieties that possess the capability of effectively converting a pro-drug to a cytotoxic drug form.

01—Transgenic Zebrafish Expressing an Ablation Product.

In an aspect, a novel transgenic zebrafish comprises a transgenic construct that facilitates the ablation of cells expressing—or cells near a cell expressing an ablation-promoting gene product encoded by the transgene. The transgenic construct utilized to create transgenic fish comprises regulatory DNA sequence operably linked to an ablation-promoting gene product sequence, the gene product being comprised of at least one component of a pro-drug conversion system.

In an aspect, the transgenic construct utilized to create the transgenic fish comprises regulatory DNA sequence operably linked to the ablation-promoting gene product sequence such that the regulatory sequence promotes expression of the gene product in at least one of a specific cell, cell type(s), and/or tissue(s).

02—Transgenic Zebrafish Co-Expressing an Ablation and a Reporter Product.

In an aspect, novel transgenic zebrafish comprise a transgenic construct that facilitates ablation of cells co-expressing, or near a cell co-expressing, an ablation-promoting gene product and a reporter gene product encoded by the transgene. The transgenic construct utilized to create the transgenic fish of this second iteration is comprised of regulatory DNA sequence operably linked to a coupled expression system of an ablation-promoting gene product and a reporter gene product, the ablation-promoting moiety comprising at least one component of a pro-drug conversion system, and the reporter moiety allowing selective detection of cells expressing the reporter moiety.

In an aspect, a transgenic construct utilized to create the transgenic fish comprises regulatory DNA sequence operably linked to the coupled expression system of an ablation-promoting gene product and a reporter gene product such that the regulatory sequence promotes expression of the gene product or gene products in at least one of a specific cell, cell type(s), and/or tissue(s).

In an aspect, a transgenic construct utilized to create transgenic zebrafish of this invention comprises regulatory DNA sequence operably linked to the gene product sequence(s) such that the regulatory sequence is active dining the specification, and/or maturation, and/or at maturity of at least one of' a specific cell, cell type(s), and/or tissue(s), and/or that the regulatory Sequence is active during all phases—initial specification, maturation, and at maturity—of a delineated cell lineage.

Moreover, in an aspect, expression of the gene product(s) is sufficiently maintained in the differentiated cell, cell type(s), and/or tissue(s) to facilitate the methods of the disclosed invention. Expression that is specifically initiated and maintained in differentiated cells and or tissues has several advantages regarding an ablation and regeneration paradigm. Most notably, this feature ensures that a regenerative cell and/or tissue expressing the transgene product represents a bona fide replacement for the cell and/or tissue that was lost; by virtue of the fact that both the ablated cell(s) and the regenerating cell(s) are considered mature cell types with distinct properties and functions. Additionally, expression that is maintained in terminally differentiated cells expands the time window available for cellular regeneration screening, as disclosed herein.

Regarding the cellular and/or tissue specific expression of an ablation-promoting in transgenic zebrafish as disclosed herein; of interest are those cells, cell types or tissues that are common to humans and zebrafish. That is, those elements of the human system that are modeled in corresponding zebrafish systems. Such systems include, but are not limited to: (i) the nervous system—e.g., retina; (ii) the vascular system; (iii) the skeletal system; (iv) muscle; (v) the enteric system—e.g., liver. Of particular interest, is expression in those cells, cell types, or tissues relevant to modeling specific degenerative diseases in zebrafish. Also of interest, is expression in specific cells, cell types, or tissues whose degeneration is thought to be causative and/or otherwise linked to the etiology and/or symptoms of a given degenerative disease. For instance, the symptoms of Parkinson's disease are believed to be caused by the loss of dopamine, more specifically the loss of dopaminergic neurons. Therefore, regulatory DNA sequences of a gene which is active in dopaminergic neurons are utilized for specific expression of a transgene product in dopaminergic neurons. Particularly useful for targeting expression in discrete neuronal subpopulations, are genes required for the biosynthesis and/or transport of neurotransmitters. Accordingly, promoter elements of the dopamine transporter (DAT) are used to specifically express transgene products in dopaminergic neurons for the purpose of creating a zebrafish model of Parkinson's disease.

03—Method of Making Transgenic Zebrafish Expressing an Ablation Product or Co-Expressing an Ablation Product and a Reporter Product.

As used herein, the term "transgenic" refers to an organism, or progeny derived from such organism(s) by gain cell transmission or cloning, that contains exogenous transgenic constructs that have been purposefully introduced into the organism. Moreover, this refers to organisms which may or may not have the introduced transgenic construct stably integrated into their genome, that is, transgenic constructs which are maintained stably and are propagated through genii cell transmission (i.e. sexual reproduction) or transgenic constructs which are expressed transiently by the organism. Furthermore, a zebrafish derived from a transgenic fish egg, sperm cell, embryo or other cell is determined to be transgenic if the transgenic fish egg, sperm cell, embryo or other cell contributes DNA to the genomic DNA of the zebrafish.

Generally speaking, transgenic zebrafish herein are derived by methods equivalent in purpose and end as those described previously (Meng et al., 1999). Briefly, a transgeuic construct is artificially introduced into a zebrafish embryo such that transgenic DNA sequences in the transgenic construct function to produce a gene product transiently in the developing fish and/or are integrated into the germline DNA of the zebrafish such that the transgene is transmitted through the genuine and a gene product is produced in progeny of the injected fish.

3a. Preferred Composition of Transgenic Constructs.

For the purpose of generating transgenic zebrafish it is understood that the transgenic construct is assembled and/or otherwise contained in any vector system for the propagation of recombinant DNA, including but not limited to, commercially available cloning vectors, viral vectors, cosmids, and artificial chromosomes.

3a. i) Regulation of Expression.

In an aspect, regulatory DNA sequences of genes which are active during the specification, maturation, and/or at maturity of a particular cell, cell type, or tissue are utilized for cell and/or tissue specific expression of a transgene product, whereby the spatial and temporal pattern of transgene expression is identical (or nearly identical) to the expression pattern of the endogenous gene product. Alternatively in an "enhancer trap" strategy, minimal regulatory elements operably linked to a reporter gene product are randomly inserted into the genome and expression patterns of interest are selected for based on expression of the reporter. Regulatory regions are typically located in the "upstream" 5-prime non-coding regions of a gene but can also be located in "downstream" 3-prime non-coding regions, in introns, and even in exons. In addition, in vertebrates it is known that some regulatory regions, typically enhancers, are located far from the coding sequence. Furthermore, the coding sequence of some genes can span equally large distances. Specificity of gene expression is typically accomplished through the topological arrangement of an ensemble of regulatory DNA regions, relative to the gene product coding sequence. Regulatory sequences often function as modular units that are associated with many different genes, and are thereby found throughout the genome of a given organism. Alternatively, a given regulatory sequence is uniquely associated with a discrete gene.

Generally speaking however, each gene has a distinct arrangement of regulatory modules such that the ensemble results in a unique spatial and temporal expression pattern of the gene product. For these reasons, when constructing a transgene intended for cell type specific expression it is generally best to avoid disrupting, as much as is possible, the overall structure of the gene whose regulatory regions are being co-opted. Moreover, it is also best to include as much sequence 5-prime and 3-prime of the coding sequence as possible. For instance, homologous recombination is used to insert the coding sequence of a transgene product directly into the genomic locus of a gene with a desired expression pattern. Artificial chromosomal (AC) libraries, whereby large intact regions of genomic DNA are propagated in bacteria (BACs, and PACs, bacteriophage P1-derived) and yeast (YACs), and bacterial recombination systems greatly facilitate this approach.

Regarding the composition and structural organization of regulatory DNA elements contained in transgenic constructs used to generate cell type specific expression patterns in novel transgenic zebrafish disclosed herein, any composition of regulatory DNA sequences that can confer a desired expression pattern of associated transgene products are considered applicable to the invention disclosed herein. In a simple case, DNA cloning procedures (e.g. restriction enzyme mediated recombination) arc used to operably link regulatory regions (e.g. 1 to 10 kb of 5-prime untranslated sequence) to the transgene product in standard cloning vectors (e.g. pBluescript). In the case where the properties of highly conserved promoter and/or enhancer elements are known it is understood that such sequences are incorporated into transgenic constructs such that they are operably linked to the transgene product in standard cloning vectors.

In an aspect, the coding sequence of the transgene product is inserted into the coding sequence of a genomic locus contained in an artificial chromosome system, the gene product of which is expressed in the desired expression pattern.

In an aspect, insertion of the coding sequence of the transgene is within the first exon, or even at the initiation methionine, of a genomic locus contained in an artificial chromosome system, the gene product of which is expressed in the desired expression pattern such that the gene product expressed from the targeted genomic locus is solely the transgene product.

In an aspect, insertion of the coding sequence of the transgene is within the first exon, preferably at the initiation methionine, of a genomic locus contained in an artificial chromosome system, the gene product of which is expressed in the desired expression pattern such that the gene product expressed from the targeted genomic locus is solely the transgene product and wherein I-Sce I sites are positioned such that the transgenic construct is excised by I-Sce I restriction enzyme digest with the majority of the 5-prime and 3-prime flanking regions of the targeted genomic locus intact.

In an aspect, the transgenic construct comprises a minimal promoter element operably linked to a co-expressed ablation-promoting and reporter transgene product such that the transgenic construct is randomly inserted and/or transposed in the genome of zebrafish using an "enhancer trap" strategy that facilitates random expression patterns that are dependent on properties of regulatory regions (e.g. enhancers and/or repressors) that act at the site of integration. For instance, enhancer trap lines are created in zebrafish using transposable elements (e.g. Sleeping Beauty, the Tcl/mariner-like family etc., Ivies et al., 1999) and fish that demonstrate expression patterns of interest are propagated and utilized identically to other transgenic zebrafish disclosed herein.

In an aspect, the transgenic construct comprises a heterologous gene product expression amplification system that is further comprised of regulatory DNA sequence operably linked to a heterologous DNA binding/activating gene product that, in turn, regulates expression of a transgene product(s) operably linked to activating sequences specific for the given binding. In particular, The Gal4-UAS system has been shown to be operative in zebrafish (Koster and Fraser, 2001; Scheer and Campos-Ortega, 1999). Moreover, such systems can be structured as co-linear DNA molecules—whereby all elements are contained in a single DNA construct—or as modular units—whereby individual elements are contained in separate DNA constructs that can be combined through co-introduction into a transgenic host and/or by deriving separate transgenic lines expressing individual modular units (or sets of modular units) that are mated to produce offspring expressing the modular units contained in each parent.

In an aspect, the transgenic construct comprises an enhancer trap system comprising a minimal promoter element operably linked to a given DNA binding protein (e.g. (Gal4-VP16 fusion) and a reporter gene product under regulation of corresponding activating sequences (e.g. UAS, upstream activating sequences specific for Gal4) such that the transgenic construct is randomly inserted and/or transposed in the genome of zebrafish using an "enhancer trap" strategy that facilitates random expression patterns that are dependent on properties of regulatory regions (e.g. enhancers and/or repressors) that act at the site of integration. For Stance, enhancer trap lines can be created In zebrafish using transposable elements (e.g. Sleeping Beauty, the Tcl/mariner-like family etc., Ivies et al., 1999) and fish that demonstrate expression patterns of interest can be propagated and utilized identically to other transgenic zebrafish disclosed herein.

In an aspect of this invention, regulatory DNA sequences which specify a desired expression pattern of operably linked gene products are derived from zebrafish sequence (i.e. homologous) and recombined with the transgene product coding sequence in standard plasmid vectors using established cloning procedures, such as restriction enzyme digest and cohesive end ligation.

In an aspect, the transgene (product coding sequence) is inserted into the coding sequence of a zebrafish genomic locus contained in an artificial chromosome system, the gene product of which is expressed in the desired expression pattern, using established cloning procedures, such as bacterial recombination.

In an aspect, regulatory DNA sequences which specify a desired expression pattern of operably linked gene products are derived from species other than zebrafish sequence (i.e. heterologous) and recombined with the transgene product coding sequence in standard plasmid vectors using established cloning procedures, such as restriction enzyme digest and cohesive end ligation.

In an aspect, the transgene (product coding sequence) is inserted into the coding sequence of a heterologous (a species other than zebrafish) genomic locus contained in an artificial chromosome system, the gene product of which is expressed in the desired expression pattern, using established cloning procedures, such as bacterial recombination.

In an aspect, regulatory DNA sequences are derived from pufferfish, "fugu" (Takifugu rubripes). The pufferfish has a condensed genome that is believed to have selectively eliminated, or perhaps never actively propagated, so-called "junk" DNA. Whatever the mechanism, the result is that regulatory DNA regions and coding sequences in pufferfish are on avenge eight times smaller than other vertebrates. By inference then it stands to reason that a given length of pufferfish regulatory DNA sequence is on average likely to contain more functional regulatory elements (elements which coordinately specif5r a restricted gene product expression pattern) than the same length of DNA from other vertebrate species.

Genomic Fugu DNA is commercially available in SAC and cosmid libraries that have been mapped to contig sequencing data. The Fugu genome can be searched for paralogs of genes with expression patterns of interest and corresponding SAC and/or cosmid vectors utilized for transgene insertion into the locus of interest. I-Sce I sites flanking the locus of interest can be engineered into the vector or generated by PCR using oligomers which add I-Sce Ito each end during amplification.

3a. ii) Composition of Ablation-Promoting Transgene Product.

As used herein, the term "ablation" includes, but is not limited to, a termination of cell metabolic functions such that the cell dies and is eliminated from the organism.

As used herein, the term "metabolic" includes the living activities of the cell.

As used herein, the term "ablation-promoting moiety" or "ablation-promoting transgene product" refers to at least one of a protein or RNA molecule. Useful ablation-promoting moieties include, but are not limited to, pro-drug converting enzymes such as bacterial nitroreductase (Denny, 2002).

As used herein, the term "pro-drug" includes, but is not limited to a pharmacologically inert chemical derivative that can be converted to an active cytotoxic drug form. Useful pro-drugs include, but are not limited to those appropriate for pro-drug converting enzymes, such as CR 1954 and metronidazole (these being substrates for bacterial nitroreductase, Bridgewater et al., 1997).

As used herein, the term "pro-drug converting system" or "pro-drug conversion system" refers to one or more moieties that possess the capability of converting a pro-drug to a cytotoxic drug form.

Pro-drug conversion systems function to convert physiologically inert pro-drugs into cytotoxic drugs which, when effectively presented to a cell at concentrations greater than or equal to a quantity sufficient for compromising cellular metabolism, rupturing the cell membrane and/or otherwise compromising the cells ability to survive, function to ablate (i.e. kill) the cell. This invention utilizes an enzyme targeted pro-drug methodology for site specific cytotoxic drug production. The pro-drug is delivered to the site of action, and the pro-drug is selectively altered resulting in the formation of an active drug which is sufficiently retained for use. Of particular relevance to transgenic expression of a pro-drug converting system, it is critical that the activity of the pro-drug converting activity is not normally present in the host organism—i.e. that the pro-drug remains inert until conversion by the transgene product. Pro-drug converting systems have been extensively developed as cancer targeting therapies whereby cancer cells can be specifically ablated (Denny, 2001). Here, we utilize genetic delivery of a pro-drug converting system in order to facilitate targeted cellular ablation in zebrafish.

Regarding the composition and structural organization of ablation-promoting trans gene products contained in transgenic constructs used to generate transgenic zebrafish; in general, any gene product or gene product activity, not normally present in the fish that facilitates the ablation of a cell expressing the gene product is considered applicable to the invention disclosed herein (i.e., is useful).

In an aspect, the ablation-promoting transgene product comprise a pro-drug converting enzyme. Useful enzymes include those which have the ability to reduce a nitro group of various p-nitrobenzyloxycarbonyl derivatives of cytotoxic compounds to give "self-emulative" compounds (pro-drugs) that automatically decompose to release cytotoxic compounds (drugs). The preferred are enzymes of bacterial or viral original with wide substrate specificity but having an activity not normally present in the fish. One illustrative nonlimiting example includes bacterial nitroreductase that can convert a relatively nontoxic monofunction alkylating agent into a cytotoxic (hypotoxic) difunctional alkylating agent. Other useful enzymes include DT diaphorase, plasmin, carboxypeptidaseG2, thymidine kinase (viral), cytosine diaminase, glucose oxidase, xanthine oxidase, carboxypeptidase A, Gamma-galactosidase, Beta-glucosidase, azoreductase, Gamma Glutantyl transferase, B-glucuronidase, Beta lactamase, alkaline phosphatase, penicillin amidase, cytochrome P-450, Horseradish peroxidase, Beta-galactosidase and nitroreductase.

In an aspect, the ablation-promoting transgene product comprises the pro-drug converting enzyme, bacterial nitroreductase. Useful nitroreductases occur naturally within the cells of *E. coli* B, *E. coli* C and other *E. coli* strains (e.g. K12 type as well as other gram-negative organisms e.g. *Thermus aquaticus*, and gram positive bacteria such as *Bacillus amyloliquifaciens* and *Bacillus caldotenax*). A useful illustrative nitroreductase is that isolated nitroreductase comprising the 217 residue, *E. coli* amino acid sequence disclosed in U.S. Pat. No. 5,633,158 (issued to Gillian Anlezark et al., on May 27, 1997 and which is incorporated herein in its entirety by reference).

3a. iii) Composition of Reporter Transgene Product.

As used herein, the term "reporter" includes, but is not limited to, a gene product that facilitates direct or indirect detection of the physical presence of a cell(s) and/or tissue(s) expressing the gene product. Useful reporters include, but are not limited to, fluorescent proteins (e.g. green fluorescent protein, GFP), bioluminescence catalyzing enzymes (e.g. luciferase) and metabolic enzymes with colorimetric substrates (e.g. beta-galactosidase).

Reporter genes facilitate the visualization of biological entities, processes and/or phenomenon. For instance, a reporter can be used simply to detect the presence and/or absence of a cell or tissue. Time-lapse imaging of cellular reporters can reveal developmental "cellular behaviors" such as cell migration patterns, neuronal outgrowth and elaboration, and cell death. The general activity of DNA regulatory elements can also be monitored using reporters as read outs for transcriptional activity. Fluorescent reporters, such as green fluorescent protein (GFP), which arc detectable without the need of secondary co-factors have revolutionized the field of biological imaging in recent years.

Regarding the composition and structural organization of reporter transgene products contained in transgenic constructs used to generate transgenic zebrafish of this invention; in general, any gene product allowing selective detection of a cell expressing the gene product is considered applicable to the invention disclosed herein. In an aspect, the reporter product allows visual detection of a reporter-expressing cell(s) by catalyzing a colorimetric reaction (e.g. beta-galactosidase).

In an aspect, the reporter product allows visual detection of a reporter-expressing cell(s) by catalyzing a bioluminescent reaction (e.g. luciferase). In an aspect, the reporter product allows detection of a reporter-expressing cell(s) in and of itself without the need for secondary co-factors and/or substrates reactions as is the case for fluorescent proteins (e.g. GFP).

3a. iv) Composition of Co-Expression System.

As used herein, the terms "coupled expression system" or "co-expression system" refer to any effective method that allows two or more functional gene products to be co-regulated such that they are necessarily expressed in identical or overlapping spatial and temporal patterns. Useful coupled expression systems include, but are not limited to, protein-protein fusion(s), and internal ribosome entry sites (IRES).

As used herein, the term "co-regulated" refers to a method that allows the expression of two or more functional gene products to be under the control of the same regulatory DNA sequence such that they are necessarily expressed in identical spatial and temporal patterns.

Coupling the expression of a reporter and a pro-drug conversion system is advantageous because it allows direct monitoring of those cells that would be effected by an addition of pro-drug—loss of reporter signifying cellular ablation. Following ablation the return of a reporter signal allows monitoring of cellular regeneration. In addition, reporters that allow real time monitoring can be used to determine the efficacy of pro-drug treatment.

Regarding the composition and structural organization of co-expression systems contained in transgenic constructs used to generate transgenic zebrafish of this invention, in general, any method that promotes coupled expression of two or more functional gene products in the same cell(s) is considered applicable to the invention disclosed herein. For instance, co-introduction or sequential addition of separate transgenes containing equivalent DNA regulatory elements but operably linked to different gene products.

In an aspect, the co-expression component comprises an internal ribosome entry site (IRES, Wang et al., 2000) positioned between independent but tandemly linked gene products, which functions to allow concurrent translation of the gene products via ribosomal entry at multiple sites along a single mRNA molecule.

In an aspect, the co-expression element is comprised of a well defined DNA regulatory protein-activation domain system (e.g. the Gal4/VPI6-UAS system, Scheer and Campos-Ortega, 1999), whereby regulatory sequences of the transgenic construct control the expression of a "driver" protein (e.g. (Gal4/VP16) capable of binding to and activating DNA transcription of "reporter" gene products operably linked to DNA sequences (e.g. upstream activating sequences, UAS) and thereby promoting the co-expression of two or more reporter gene products operably linked to a upstream activating sequences specific to the "driver" protein.

In an aspect, co-expression is obviated by fusing two or more gene products such that they are now encoded by a single contiguous DNA sequence and whereby each element of the fusion product retains the function normally associated its expression. For instance, a GFP-Nitroreductase fusion product (Medico et al., 2001). In addition, in some instances single proteins (e.g. CytoCy5, from Amersham) can act as both reporter and ablation-promoting element (Ismail et al., 2001).

3a. v) Composition of Co-Expressed Ablation-Promoting and Reporter Transgene Product Regarding the composition and structural organization of co-expressed transgene products comprised of an ablation-promoting gene product and reporter gene product and contained in a transgenic construct used to generate these novel transgenic zebrafish; in general, any coupled expression system of an ablation-promoting gene product and reporter gene product facilitating both the ablation of a cell expressing the coupled gene products and allowing selective detection of a cell expressing the coupled gene products is considered applicable to the invention disclosed here. For clarity the following aspects are presented in pairs of both elements of the coupled expression system—as co-expressed ablation-promoting element and reporter element pairs—however, it is understood that the individual components are fully modular and that any combinatorial composition of the individual elements is considered applicable to the invention disclosed herein.

In an aspect, the ablation-promoting transgene product of the co-expression system comprises a pro-drug converting moiety and that the reporter transgene product of the co-expression system allows visual detection of reporter-expressing cell(s) by catalyzing a colorimetric reaction (e.g. beta-galactosidase).

In an aspect, the ablation-promoting transgene product of the co-expression system comprise a pro-drug converting enzyme and that the reporter transgene product of the co-expression system allow visual detection of reporter-expressing cell(s) by catalyzing a bioluminescent reaction (e.g. luciferase).

In an aspect, the ablation-promoting transgene product of the co-expression system comprises a pro-drug converting enzyme, nitroreductase and the reporter transgene product of the co-expression system allows visual detection of reporter-expressing cell(s) in and of itself without the need for co-factors and/or substrates reactions, as is the case for fluorescent proteins (e.g. GFP). In addition, the ablation-promoting and reporter protein can be one and the same (e.g. CytoCy5).

3b. Method of Making Transgenic Zebrafish.

In an aspect, transgenic constructs are introduced by microinjection into zebrafish cells, preferably single cell stage zebrafish embryos, in order to derive transgenic fish. After introduction of the transgenic construct into embryonic cells, the embryo is allowed to develop until such time as is appropriate to screen for the presence of the transgene. In the ease where the injected transgenic DNA construct contains no reporter product, PCR can be used to screen fish for the presence of the transgene. For instance, a small clipping from the tail of young adult fish can be collected and processed for the presence of the transgene product using PCR oligomers specific for sequence in the transgene. In the case where a reporter gene product is used expression of the transgene can be screened for visually. For instance, zebrafish larvae that were previously injected with a GFP containing transgene can be screened using a fluorescent microscope to identify fish that express GFP.

In an aspect, transgenic zebrafish are raised to maturity and subsequently screened; first for germline transmission of the transgene, i.e. for the ability to produce transgene-expressing progeny and, second for desired cellular expression patterns of the transgene in transgene-expressing progeny. Many methods for introducing the transgenic construct exist, all such methods are considered applicable to this disclosure. Such methods include but are not limited to, introducing the transgenic construct into embryonic fish cells by microinjection, electroporation, particle gun bombardment, viral infection and through the use of liposomes. Moreover, several alternative compositions of the structure and/or co-factors of the transgenic construct introduced have been developed which increase the frequency of genomic integration and/or germline transmission of the transgenic construct. All such variations of composition and/or matter are considered applicable to this disclosure.

Regarding methods used to introduce transgenic constructs into zebrafish for the creation of transgenic fish of this invention: in general, any method that succeeds in introducing a transgenic DNA construct into zebrafish such that regulatory DNA sequences in the transgenic construct function to produce a transgene product in at least one of a specific cell, cell type(s), and/or tissue(s) in the zebrafish, or in the progeny of the zebrafish that bad a transgenic construct introduced, is considered applicable to the invention disclosed herein.

In an aspect, the transgenic construct is introduced by microinjection into an embryonic zebrafish cell, and more preferentially into the single cell stage zebrafish embryo.

In an aspect, a large volume of solution containing the transgenic construct (1 to 1.5. nl) is microinjected into the single cell stage zebrafish embryo in order to increase the percentage of injected fish that have integrated the transgenic construct into the germline and are therefore capable of producing transgenic progeny.

Regarding the structural topology of the transgenic construct introduced into zebrafish for the purpose of creating transgenic zebrafish. In general, the transgenic DNA construct introduced can be in any physical conformation (e.g. circular plasmid or linear molecule).

In an aspect, transgenic constructs are introduced as linear DNA molecules. Linearization can accomplished by restriction enzyme digest of the transgenic construct with restriction sites that flank the DNA to be introducted. This structural arrangement can either be engineered into the plasmid vector containing the transgenic construct, or can be introduced using PCR oligomers to amplify the transgenic construct before insertion into the plasmid. Alternatively the transgenic construct can be linearized by directly amplifying the transgenic DNA construct by PCR.

In an aspect, transgenic constructs wherein the regulatory DNA sequences, are operably linked gene product(s) and corresponding expression-promoting sequences are flanked by recognition sequences for I-Sce I restriction enzyme digestion—this structural arrangement can either be engineered into the plasmid vector containing the transgenic construct or can be engineered into PCR oligomers used to amplify the transgenic construct—such that the linearized transgenic DNA construct is the result of I-Sce I restriction enzyme digestion of a circular plasmid or a PCR fragment digested with I-Sce I enzyme.

Regarding the species of fish utilized to create transgenic fish herein: Any strain and/or variety (inbred or otherwise) of commonly available laboratory or commercially available fish that can be used to generate effective transgenic fish lines is considered applicable to the invention disclosed herein and covered by the claims presented.

In an aspect, in order to facilitate cloning of specific genetic mutations transgenic zebrafish are derived from inbred lines (e.g. SJD, C32, and WIK etc.).

In an aspect, in order to facilitate visualization of cells and tissues transgenic zebrafish are derived from "non-pigmented" mutant zebrafish substantially devoid of melanophore deposition (e.g. albino mutants) and irridiphore deposition (e.g. roy orbison, transparent mutants), or from zebrafish substantially devoid of both melanophore and irridiphore deposition (e.g. alb; roy double mutants). "Non-pigmented" mutants extend the time window available for observing cells and/or tissues that reside in the interior of the fish, especially with regard to reporter protein detection, such that adult fish can be more readily utilized for the screening methods disclosed herein. In addition, "non-pigmented" zebrafish do not require the addition of potentially deleterious pigment blocking factors (e.g. 0.003% 1-phenyl-2-thiourea, PTU) that are used for the visualization of deep tissues beyond the first day of development in wildtype fish.

In an aspect, transgenic zebrafish are derived from an inbred line of "non-pigmented" zebrafish mutant lines. However, it should be noted that "non-pigmented" zebrafish lines may be more prone to physical damage than wildtype clutch mates which may impact the practicality of utilizing such lines for the invention disclosed herein, especially with regard to mutagenesis screening.

3b. i) Method of Making Transgenic Fish Expressing an Ablation-Promoting Transgene Product Only.

In an aspect, transgenic fish expressing an ablation-promoting transgene product (only) are derived using the methods aspects and embodiments detailed above (3b) with the following additional modifications:

Regarding the composition and structural organization of transgenic constructs comprised of transgenic DNA sequences which capably and competently regulate the expression of and encode an ablation-promoting transgene product that is utilized to create these novel transgenic fish; in general; any transgenic construct that functions to express an ablation-promoting transgene product in a desired expression pattern is considered applicable to the invention disclosed herein. In the simplest case, DNA cloning procedures (e.g. restriction enzyme mediated recombination) can be used to operably link regulatory regions (e.g. 1 to 10 kb of 5-prime untranslated sequence) to an ablation-promoting transgene product in standard cloning vectors (e.g. pBluescript). In the case where the properties of highly conserved promoter and/or enhancer elements are known it is understood that such sequences can be incorporated into transgenic constructs such that they are operably linked to an ablation-promoting transgene product in standard cloning vectors.

In an aspect, it is preferred that the coding sequence of an ablation-promoting transgene product is inserted into the coding sequence of a genomic locus contained in an artificial chromosome system, the gene product of which is expressed in the desired expression pattern.

In an aspect, a coding sequence of an ablation-promoting transgene product comprises a pro-drug converting moiety which is inserted into the coding sequence of a genomic locus contained in an artificial chromosome system, the gene product of which is expressed in the desired expression pattern.

In an aspect, a coding sequence of an ablation-promoting transgene product comprised of a pro-drug converting enzyme is inserted within the first exon, or even at the initiation methionine, of a genomic locus contained in an artificial chromosome system, the gene product of which is expressed in the desired expression pattern such that the gene product expressed from the targeted genomic locus is solely the transgene product.

In an aspect, an ablation-promoting transgene product comprised of the pro-drug converting enzyme, bacterial nitroreductase is inserted within the first exon, or even at the initiation methionine, of a genomic locus contained in an artificial chromosome system, the gene product of which is expressed in the desired expression pattern such that the gene product expressed from the targeted genomic locus is solely the transgene product and wherein I-Sce I sites are positioned such that the transgenic construct can be excised by I-Sce I restriction enzyme digest with the majority of the 5-prime and 3-prime untranslated regions of the targeted genomic locus left intact.

3b. ii) Method of Making Transgenic Fish Co-Expressing an Ablation-Promoting Transgene Product and a Reporter Transgene Product.

Transgenic fish co-expressing an ablation-promoting transgene product and a reporter transgene product will be derived using the methods, aspects and embodiments detailed above (3b) with the following modifications:

Regarding the composition and structural organization of transgenic constructs comprised of transgenic DNA sequences which regulate the coupled expression of and encode an ablation-promoting transgene product and a reporter transgene product that is utilized to create transgenic fish of this invention; in general, any transgenic construct that functions to co-express an ablation-promoting transgene product and a reporter transgene product in a desired expression pattern is considered applicable to the invention disclosed herein.

In a simple case, DNA cloning procedures (e.g. restriction enzyme mediated recombination) can be used to operably link regulatory regions (e.g. 1 to 10 kb of 5-prime untranslated sequence) to a coupled expression system, comprised of an ablation-promoting transgene product and reporter transgene product, in standard cloning vectors (e.g. pBluescript).

In the instance where the properties of highly conserved promoter and/or enhancer elements are known it is understood that such sequences can be incorporated into transgenic constructs such that they are operably linked to a coupled expression system, comprised of an ablation-promoting transgene product and reporter transgene product, in standard cloning vectors, For clarity the following aspects arc presented in sets of the three novel operably linked elements of the transgenic construct—the regulatory DNA element, ablation-promoting element, and reporter element—however, it is understood that the individual components are fully modular and that any alternative combinatorial composition individual elements is considered applicable to the invention disclosed herein.

In an aspect, a coupled expression system, comprising a pro-drug converting moiety and a reporter that allows visual detection of reporter-expressing cell(s) by catalyzing a colorimetric reaction (e.g. beta-galactosidase), is inserted into the coding sequence of a genomic locus contained in an artificial chromosome system, the gene product of which is expressed in the desired expression pattern.

In an aspect, a coding sequence of a coupled expression system—comprised of an ablation-promoting pro-drug converting enzyme and a reporter that allows visual detection of reporter-expressing cell(s) by catalyzing a bioluminescent reaction (e.g. luciferase) is inserted within the first exon, or even at the initiation methionine, of a genomic locus contained in an artificial chromosome system, the gene product of which is expressed in the desired expression pattern, and such that the gene product expressed from the targeted genomic locus is solely the transgene product.

In an aspect, coding sequence of a coupled expression system, comprised of the ablation-promoting pro-drug converting enzyme, bacterial nitroreductase and a reporter that allows visual detection of reporter-expressing cell(s) without the need for co-factors and/or substrates reactions (e.g. GFP) is inserted within the first exon, or even at the initiation methionine, of a genomic locus contained in an artificial chromosome system, the gene product of which is expressed in the desired expression pattern such that the gene product expressed from the targeted genomic locus is solely the transgene product and wherein I-Sec I sites are positioned such that the transgenic construct can be excised by I-Sec I restriction enzyme digest with the majority of the 5-prime and 3-prime untranslated regions of the targeted genomic locus left intact.

While the invention has been described in terms of various specific embodiments, the invention can be practiced with modifications which remain within the spirit and scope of this discovery. It is believed that an optimal method of transgene insertion would be targeted site-specific recombination into the zebrafish genome—akin to the process of knock-out and knock-in technology in mice.

04—Methods for Targeted and Regional Ablation in Zebrafish Expressing an Ablation Product or Co-Expressing an Ablation Product and a Reporter.

Cellular ablation can be accomplished by several different techniques—photo-ablation, general toxin application, laser (heat and photo) ablation, and pro-drug conversion being just a few. Pro-drug converting systems have the following advantages: i) specificity, pro-drug converting moieties can be specifically targeted to discrete cells or cell types; ii) cost, many pro-drugs are common pharmaceutical reagents that are cheap and readily available; iii) well described, many enzyme/pro-drug combinations have been thoroughly investigated and specific properties described; iv) treatment with pro-drug can be temporally regulated; v) ease of application of pro-drug to huge numbers of organisms simultaneously permitting high-volume (aka high-throughput) applications.

Pro-drug converting moieties function to convert physiologically inert pro-drugs into cytotoxic drugs which, when present in or presented to a cell at concentrations greater than or equal to a quantity sufficient for compromising the metabolism, rupturing the membrane and/or otherwise compromising the cells ability to survive, function to ablate (i.e. kill) the cell. Without being bound by theory, it is generally believed that cellular ablation by action of the cytotoxic drug occurs through compromised cellular metabolism and/or by disruption of the cell membrane. However, any other mechanism whereby a cytotoxic drug generated by pro-drug conversion functions to ablate a cell is considered applicable to the invention disclosed herein.

In an aspect, a useful drug has a cytotoxicity greater than that of the pro-drug. Typically, the pro-drug has an enzyme cleavable covalent link between a drug and a chemical moiety associated therewith although some useful moieties of pro-drug include the salt form of an active drug molecule. Typically a partly or essentially water soluble salt form would be employed, including those moieties wherein there is a covalent link between a drug and chemical moiety and includes salts of the pro-drug such as those which are moderately or highly water soluble such as alkali metals, ammonium and amine salts and alkaline earth metal salts.

Useful non-limiting alkali metals include sodium and potassium. Useful alkaline earth metals include calcium and magnesium. Useful amine salts include isopropyl amine, butyl amine and isobutyl amine and derivatives thereof.

Typical non-limiting useful pro-drugs include 5-(aziridine-1-yl)-2,4-nitrobenzamide, peptidyl-p-phenylenediamine-mustard, benzoic acid mustard plutamates, g6-methoxypurine arabinonucleoside, 5-fluorocytosie, glucose, hypoxanthine, methotrexate-alane, N-(94-(-D-galactopyranosyl), benzyloxycarbonyl)-daunorubicine, amygdalin, azobenzene mustards, gamma-glutamyl-p-phenylenediamine mustard, phenolmustard-glucuronide, epirubicin-glucuronide, vinca-cephalosporin, nitrogen-mustard-cephalosporin, phneolmustard phosphate, doxorubicine phosphate, mitomycin phosphate, etoposide phosphate, palytoxin-4-hydroxyphenyl-acetamide, coxonubicin-phenoxyacetanide, cyclophosphamide isofamide and 4-nitrobenzyloxycarbonyl derivatives.

Typical useful non-limiting drugs include S-(aziridin-1-yl)-4-hydroxyl-amino-2-nilrobenzamide, phenylenediamine-mustard, benzoic acid mustards, gganeiclovir triphosphate, adenine arabinonucleoside, triphosphate (araATP), 5-fluoroouracid, hydrogen peroxide, superoxide, hydrogen peroxide, methotrexate, daunorubicin, cyanide, phenyelendiamine mustards, phenyldiamine mustard, phneolmustard, epirubicin, 4-desacetylvinblastine-3-carboxyhydrazide, phenylenediamine mustard, nitrogen mustards, phneolmustard, doxorubicin, mitomycin alcohol, etoposide, palytoxin, doxorubicin, melphalan, phosphoamide mustard (+acrolein), 5-(aziridin-1-yl)-4-hydroxylamino-2-nitrobenzamine, e.g. actinomycin D and mitomycin C.

4a. Targeted Ablation.

In an aspect, targeted cellular ablation is induced in transgenic zebrafish expressing an ablation-promoting gene product whereby only cells competent for pro-drug conversion, that is a cell specifically expressing pro-drug converting moieties, are eliminated from the transgenic zebrafish. In the case where pro-drug converting moieties are specifically expressed within a distinct cell, cell type, or tissue of a transgenic zebrafish, targeted cellular ablation is induced when an appropriate pro-drug is presented as by manual addition of a pro-drug to a solution containing the transgenic fish so that the cells of the transgenic zebrafish are exposed at a concentration sufficient for the specific demise of the cell(s) expressing the pro-drug converting gene product, but at a concentration below a level that would cause general toxicity to cells that are not expressing the transgene. It should be noted that the cellular specificity of the cytotoxic effect is generally determined by the concentration of the pro-drug presented to, and thereby the quantity of cytotoxic drug produced by, a cell competent for pro-drug conversion. However, targeted cellular ablation can also result from inherent properties of the cytotoxic drug produced wherein the drug is only capable of promoting ablation of cells that produce the drug intrinsically but not cells that extrinsically contact the drug (e.g. metronidazole).

The targeted ablation paradigm disclosed herein represents a "cellular knock-out" approach to understanding cellular and/or organ system biology. Of particular interest are applications of our invention to studies of nervous system function. Historically, brain lesions caused by injury or disease have allowed an assessment of the function of fairly well circumscribed brain regions. Experimentally, using model organisms a finer level of control is afforded and surgical lesions have been used to verify and more accurately localize the function of specific brain regions in vertebrates. However, the ability to precisely remove discrete elements of a given neural circuit, would facilitate a much finer dissection of nervous system function. The targeted cellular ablation system disclosed in this invention provides a versatile research tool to this experimental paradigm.

4a. i) Preferred Composition of Pro-Drug Utilized for Targeted Cellular Ablation in Transgenic Fish.

As used herein, the term "pro-drug" includes a pharmacologically inert chemical derivative that can be converted to an active cytotoxic drug form, enzymatically or nonenzymatically. Useful non-limiting pro-drugs include, but are not limited to those appropriate for pro-drug converting enzymes, such as metronidazole (this being a substrate for bacterial nitroreductase). Such useful drugs include but are not limited to, latientated, bioreversible derivate or cogoner drugs, that are pharmacologically inactive forms of a drug.

Regarding the structure and composition of the pro-drug utilized for targeted cellular ablation in the novel transgenic fish: In general, any biologically inert compound that can be converted to a cytotoxic form by action of a pro-drug converting moiety is considered applicable to our discovery herein, In an aspect, the pro-drug is water soluble or substantially water soluble and readily absorbed by zebrafish.

In an aspect, the pro-drug is a water soluble compound readily absorbed by zebrafish that is cytotoxic to only those cells expressing an appropriate pro-drug converting moiety—i.e. having targeted cell-specific cytotoxic properties. Of particular interest are water soluble pro-drugs readily absorbed by zebrafish having targeted cytotoxic properties when converted by bacterial nitroreductase but which have no general toxic effect in zebrafish (e.g. metronidazole, Lanzky and Hailing-Sørensen, 1997).

4a. ii) Preferred Methods of Targeted Cellular Ablation in Transgenic Fish.

In general, any method of employing a genetically directed ablation-promoting system such that a spatially restricted pattern(s) of targeted cellular ablation can be induced is considered applicable to this invention. In an aspect, a pro-drug converting system is employed, wherein the applied pro-drug is a water soluble compound readily absorbed by fish and such that targeted cellular ablation can be induced upon presentation of the pro-drug to a cell expressing an appropriate pro-drug converting moiety.

In an aspect, a pro-drug converting system is employed wherein the applied pro-drug comprises a water soluble compound readily absorbed by fish and such that a spatially restricted pattern(s) of targeted cellular ablation is induced upon presentation of the pro-drug to a cell expressing an appropriate pro-drug converting moiety by virtue of the fact that the cytotoxic drug produced from the pro-drug has the general property of promoting targeted cellular ablation and the concentration of cytotoxic drug produced is sufficient for the specific demise of the cell(s) expressing the pro-drug converting gene product, but at a concentration below a level that would cause general toxicity to cells that are not expressing the transgene.

In an aspect, a bacterial nitroreductase-based pro-drug converting system utilizing metronidazole as the pro-drug is employed wherein the applied metronidazole is a water soluble compound readily absorbed by fish and such that a spatially restricted pattern(s) of targeted cellular ablation is induced upon presentation of metronidazole to a cell expressing bacterial nitroreduetase. The drug produced following metronidazole conversion being unable of crossing the cellular membrane thereby limiting its effect to only those cells that express nitroreductase (i.e. those cells that can convert metronidazole into a cytotoxic drug).

4b. Regional Ablation.

In an aspect, regional cellular ablation is induced in transgenic zebrafish expressing an ablation-promoting gene product whereby cells in the general vicinity of a cell producing a cytotoxic drug are also eliminated from the transgenic zebrafish. In the case where pro-drug converting moieties arc specifically expressed within a distinct cell, cell type, or tissue of a transgenic zebrafish, regional cellular ablation is induced when an appropriate pro-drug is presented to a cell expressing a pro-drug converting moiety at a concentration exceeding that required for targeted cell specific ablation, whereby excess cytotoxic drug is produced and wherein the excess drug comes into contact with neighboring cells at a concentration sufficient for ablation of these cells, and/or when the specific pro-drug presented and/or the specific cytotoxic drug produced has the property of promoting the bystander effect, a priori.

The regional ablation paradigm disclosed herein represents an "injury model" approach to understanding cellular and/or organ system biology. Many degenerative states are in fact initiated by injury to cells and/or tissues that have no inherent ability to regenerate or repair. Of particular interest are applications of this strategy to studies of nervous system injury, such as spinal cord damage. Experiments in the majority of vertebrate nervous system injury models are limited to measuring acute responses, progression and extent of degeneration and/or regeneration, and effects of therapeutic intervention. The regional cellular ablation system disclosed in this invention, by virtue of being embodied in the zebrafish system, adds to this list a genetics-based approach to this experimental paradigm. Mutagenesis screening performed in zebrafish at "saturation" levels, wherein every gene is mutated at multiple independent sites to the degree that at least one loss of function lesion is ensured at every locus, will elucidate the genetic factors that are required for a regenerative response to discrete injury paradigms.

4b. i) Preferred Composition of Pm-Drug Utilized for Regional Cellular Ablation in Transgenic Fish.

Regarding the structure and composition of the pro-drug utilized for regional cellular ablation in these novel transgenic fish. In general, any biologically inert compound that can be converted to a cytotoxic form by action of a pro-drug converting moiety is considered applicable to this invention.

In an aspect, the pro-drug is water soluble and readily absorbed by zebrafish.

In an aspect, water soluble pro-drugs readily absorbed by zebrafish are cytotoxic to those cells expressing an appropriate pro-drug converting moiety as well as those cells in the general vicinity of cells expressing an appropriate pro-drug converting moiety—i.e. the drug produced has regional ablation cytotoxic properties.

In an aspect, water soluble pro-drugs are readily absorbed by zebrafish that are converted by bacterial nitroreductase and have regional cytotoxic properties (e.g. CB1954).

4b ii) Preferred Methods of Regional Cellular Ablation in Transgenic Fish.

In general, any method of employing a genetically directed ablation-promoting system such that a spatially restricted pattern(s) of regional cellular ablation can be induced is considered applicable to this invention.

In an aspect, a pro-drug converting system is used wherein the applied pro-drug is a water soluble compound readily absorbed by fish and such that regional cellular ablation can be induced upon presentation (as by manual addition of the pro-drug into a solution containing transgenic zebrafish) of the pro-drug to a cell expressing an appropriate pro-drug converting moiety.

In an aspect, a pro-drug converting system is used wherein the applied pro-drug is a water soluble compound readily absorbed by fish and such that a spatially restricted pattern(s) of regional cellular ablation is induced upon presentation (as by manual addition of the pro-drug into a solution containing transgenic zebrafish) of the pro-drug to a cell expressing an appropriate pro-drug converting moiety by virtue of the fact that the cytotoxic drug produced front the pro-drug has the general property of promoting regional cellular ablation such that the concentration of cytotoxic drug produced is sufficient for the specific demise of the cell(s) expressing the pro-drug converting gene product and nearby cells that are not expressing the transgene.

In an aspect, a bacterial nitroreductase-based pro-drug converting system is employed utilizing CB1954 as the pro-drug. Wherein the applied CB1954 is a water soluble compound readily absorbed by fish and such that a spatially restricted pattern(s) of regional cellular ablation is induced upon presentation (as by manual addition of the pro-drug into a solution containing transgenic zebrafish) of CR 1954 to a cell expressing bacterial nitroreductase. The drug produced following CR1954 conversion having the general property of crossing cellular membranes and thereby promoting ablation of cells in the general vicinity of cells that express nitroreductase (i.e. those cells that can convert CB1954 into a cytotoxic drug)—this effect being known as the "bystander effect" (Bridgewater et al., 1997).

05—Uses for Ablation in Zebrafish Expressing an Ablation-Promoting Product or Co-Expressing an Ablation-Promoting Product and a Reporter.

Zebrafish have a remarkable capacity for cellular regeneration. Studies have established that the nervous system (Becker et al., 1997; Cameron and Carney, 2000; Vihtelic and Hyde, 2000), heart (Poss et al, 2002), fin (Poss et al., 2003), muscle (Rowlerson et al., 1997), liver (Burkhardt-Holm et al., 1999), and kidney (Reimschussel, 2001) are all capable of regeneration in zebrafish. This fact combined with the possibility of doing large scale mutagenesis and high-throughput pharmacological screening in zebrafish, denotes an unprecedented opportunity to assemble the genetic circuitry of cellular regeneration in a vertebrate model system and to increase the pace of identifying, developing, and ultimately providing beneficial therapies fur degenerative diseases.

Novel transgenic fish (disclosed herein) expressing an ablation-promoting transgene product, or co-expressing an ablation-promoting product and a cellular reporter product, provide an in vivo model for high-throughput genetic and pharmacological screens that aim to identify genes that influence the process of cellular regeneration and regeneration-promoting compounds that represent potential therapies for degenerative disorders. In addition, such fish provide an experimental model system for the study of cell and/or tissue function; ablation of specific cells, cell types, and/or tissues facilitates analyses aimed at revealing the physiological consequence of eliminating a targeted cell or tissue and thereby determining the function of the cell or tissue removed.

5a. Regeneration Studies.

A generalized protocol for ablation and subsequent regeneration screening in our novel transgenic zebrafish comprises: 1) Transgenic expression of an ablation-promoting moiety in a cell type specified by discrete regulatory regions which are uniquely active during the specification, and/or maturation, and/or at maturity of the given cell, cell type, or tissue; 2) Introduction (as by manual addition of the pro-drug into a solution containing transgenic zebrafish) of a pro-drug into embryonic, larval, or adult transgenic zebrafish such that the pro-drug is presented to an appropriate pro-drug converting moiety produced by transgene expressing cells; 3) Conversion of the pro-drug to its cytotoxic form by action of the pro-drug converting moiety; 4) Ablation of cells exposed to a sufficient concentration of the cytotoxic drug produced upon pro-drug conversion; 5) Verification of cellular ablation by an outwardly detectable cell loss, an outwardly or otherwise detectable phenotypic change and/or a detectable loss of reporter product signal; 6) Subsequent removal of the pro-drug and/or its cytotoxic derivative(s) from the embryonic, larval, or adult transgenic zebrafish; 7) An initial assessment of any evidences of cellular regeneration by. observation of outwardly visible regenerating cells, remission of a phenotypic change induced upon cellular ablation, and/or by the return of reporter product signal (e.g. cells which "reappear" having gross morphological features of those cells which were ablated will be considered to be regenerative in origin); 8) Verification of cellular regeneration by the detection of morphological, physiological, cellular, molecular, and/or any other functional hallmarks that are definitively associated with the cell type that was ablated, in cells that were generated following the ablation of the target cells. Generally speaking, in an effort to define genes and compounds that promote cellular regeneration genetic and pharmacological factors are tested for the ability to influence steps 7 and 8 in this process (immediately above).

Subsequent regeneration-based assays can be conducted in phases of primary, secondary, tertiary, etc., which become progressively more detailed in terms of defining the degree to which "replacement" cell(s) display hallmarks of the ablated cell(s), and/or tissue(s). In addition, high volume (a.k.a., high-throughput) methods can be applied in early phases to increase screening efficiency. For automated screening, fish embryos, larvae and/or adults can be arrayed in multi-well formats or passed sequentially through optical devices capable of sensing the reporter gene product and/or a detectable byproduct of reporter gene product activity. For instance, when transgenic fish express a fluorescent reporter gene product, a fluorescence activated flow cytometer—capable of sorting living zebrafish, such as the COPAS machine from Union Biometrica—can be used to determine: 1) That zebrafish express the reporter and are thereby transgenic; 2) That transgenic zebrafish lose expression of the reporter after cells co-expressing an ablation-promoting gene product and the fluorescent reporter come into contact with and convert a pro-drug into its cytotoxic form. 3) That transgenic fish that previously lost expression of the fluorescent reporter—after cells co-expressing an ablation-promoting gene product and the fluorescent reporter come into contact with and convert a pro-drug into its cytotoxic form and following removal of the pro-drug and its cytotoxic derivatives—either regenerate cells expressing the reporter gene product or do not regenerate detectable reporter gene product expression. Thus, transgenic fish co-expressing an ablation-promoting moiety and a reporter moiety greatly facilitate automated screening procedures. The ability to automate aspects of the screening process greatly reduces the time and resources required to get from disease model to therapeutic target.

5b. Ablation Studies.

In addition to providing insight into the process of cellular regeneration, transgenic fish expressing an ablation-promoting moiety facilitate studies designed to ascertain the physiological consequences of removing specific cells, cell types, and/or tissues from an organism at specific time points. Such studies can be with respect to the function of a given organ system or to the organism as a whole.

A generalized protocol for ablation studies in transgenic zebrafish includes: 1) Transgenic expression of an ablation-promoting moiety in a cell type specified by discrete regulatory regions which are uniquely active during the specification, and/or maturation, and/or at maturity of a given cell, cell type, or tissue; 2) Introduction (as by manual addition of the pro-drug into a solution containing transgenic zebrafish) of a pro-drug into embryonic, larval, or adult transgenic zebrafish such that the pro-drug is presented to an appropriate pro-drug converting moiety produced by transgene expressing cells; 3) Conversion of the pro-drug to its cytotoxic form by action of the pro-drug converting moiety; 4) Ablation of cells exposed to a sufficient concentration of the cytotoxic drug produced upon pro-drug conversion; 5) Verification of cellular ablation by an outwardly detectable cell loss, a detectable phenotypic change and/or a detectable loss of reporter product signal; 6) Assessment of the physiological consequences of having ablated the targeted cells.

In those cases where the zebrafish has a robust capacity for regeneration of the targeted cell or tissue it may be necessary to serially administer the pro-drug in order to promote complete cellular ablation. However, in general the pro-drug and cytotoxic derivatives are removed (following step 5 immediately above) in order to reduce the possibility of complications due to non-specific effects. Alternatively, high concentrations of pro-drug can be applied briefly and removed after a defined exposure time (e.g. 1 hour) in order to speed the pace of cellular ablation.

06—Specific Uses for Ablation in Zebrafish Expressing an Ablation-Promoting Product or Co-Expressing an Ablation-Promoting Product and a Reporter Product.

Zebrafish provide a vertebrate model system uniquely suited to high-throughput approaches to both genetic analyses and drug compound screening. The transgenic fish of this invention provide a unique model system for high-throughput genetic dissection of the process of cellular regeneration and high-throughput compound screening for discovery of drugs capable of promoting cellular regeneration.

Two main genetic approaches—"forward" (where a given characteristic, or phenotype, is investigated via a mutational analysis and mutated genes that impact the phenotype are subsequently identified) and, "reverse" (where a given gene is manipulated and the resultant phenotype is evaluated)—are available for genetic screens. Reverse genetics then emphasizes genes first and biological consequence secondarily. In order to emphasize a particular biological process using reverse genetics one must rely on previous knowledge in order to determine which genes to target. The power of forward genetic screens lies in the unbiased nature of the approach and in the ability to identify numerous genetic factors that impact a given biological process, thus promoting the characterization of previously unknown genetic factors and serving to reveal complete genetic circuits. Zebrafish have been established as a model genetic organism that have the benefit of being the only economical vertebrate model amenable to forward genetics so far established. The zebrafish genome sequencing project is nearing completion and the pace of identifying genetic mutations in zebrafish is steadily increasing. In addition, ex vivo development and transparency of embryonic and larval stages provide unparalleled visual analysis of developmental and biological processes. Finally, zebrafish—like most teleosts—have a remarkable capacity for cellular regeneration. Thus, for the first time the genetic circuitry of cellular regeneration can be investigated at the whole genome level.

6a—Determining the Inherent Regenerative Capacity of Transgenic Zebrafish.

A method is provided for determining the inherent regenerative capacity of zebrafish with respect to specific cells or tissues and/or following a modeled injury. In connection therewith, a generalized protocol for cellular ablation and subsequent regeneration screening in transgenic zebrafish of this invention includes: 1) Transgenic expression of an ablation-promoting moiety—or co-expressing an ablation promoting and a reporter gene product—in a cell type specified by discrete regulatory regions which are uniquely active during the specification, and/or maturation, and/or at maturity of the given cell, cell type, or tissue; 2) Introduction of a pro-drug into embryonic, larval, or adult transgenic zebrafish such that the pro-drug is presented to an appropriate pro-drug converting moiety produced by transgene expressing cells; 3) Conversion of the pro-drug to its cytotoxic form by action of the pro-drug converting moiety; 4) Ablation of transgene expressing cells—and/or ablation of transgene expressing and nearby cells via the "bystander effect" (in the case of a modeled injury)—when such cells are exposed to a sufficient concentration of the cytotoxic drug produced upon pro-drug conversion; 5) Verification of cellular ablation by detection of an outwardly visible cell loss, an outwardly or otherwise detectable phenotypic change, cytochemical methods that label dead or dying cells and/or necrotic tissue, any other indications of an induced cellular loss, and/or a detectable loss of reporter product signal; 6) Subsequent removal of the pro-drug and/or its cytotoxic derivative(s) from the embryonic, larval, or adult transgenic zebrafish; 7) An initial assessment of any evidences of cellular regeneration by, observation of outwardly detectable regenerating cells, remission of a phenotypic change induced upon cellular ablation, any other indications of repairing the induced cellular loss and/or by the return of reporter product signal; 8) Verification of cellular regeneration by the detection of morphological, physiological, cellular, molecular, and/or any other functional hallmarks that are definitively associated with the cell type that was ablated, in cells that were generated following the ablation of the target cells.

Subsequent regeneration-based assays can be conducted in phases of primary, secondary, tertiary, etc., which become progressively more detailed in terms of defining the degree to which "replacement" cell(s) display hallmarks of the ablated cell(s), and/or tissue(s). In addition, high volume (a.k.a., high-throughput) screening methods can be applied in early phases to increase efficiency. For automated screening, fish embryos, larvae and/or adults can be arrayed in multi-well formats or passed sequentially through optical devices capable of sensing the reporter gene product and/or a detectable byproduct of reporter gene product activity. The ability to automate aspects of the screening process greatly reduces the time and resources required to get from disease model to therapeutic target.

In an aspect, the zebrafish has an inherent capacity for regeneration of the ablated cell(s)s or tissue(s) and/or following the modeled injury as determined by outwardly detectable regenerating cells, remission of a phenotypic change induced upon cellular ablation that can be attributed to the presence of regenerating cells, any other indications of repairing the induced cellular loss and/or by the return of reporter product signal. In such cases the zebrafish is determined to be regeneration-competent with respect to the specific cell(s) and/or tissue(s) that were ablated.

In an aspect, the zebrafish has an inherent capacity for regeneration of the ablated cell(s)s or tissue(s) and/or following the modeled injury as determined by the absence of outwardly visible regenerating cell; a lack of remission of a phenotypic change induced upon cellular ablation, no other indications of repairing the induced cellular loss and/or no detectable return of reporter product signal. In such cases the zebrafish is determined to be regeneration-deficient with respect to the specific cell(s) and/or tissue(s) that were ablated.

In a further aspect, transgenic zebrafish undergoing cellular ablation and subsequent regeneration screening express an ablation-promoting gene product alone: In those cases where cellular ablation results (or would be expected to result) in an outwardly detectable phenotype—such as a behavioral change, a cellular loss detectable by eye or by standard light microscopy and/or by employment of a cytochemical technique for labeling dead or necrotic cells and tissues—it is possible to utilize transgenic zebrafish expressing an ablation-promoting product only for cellular regeneration screens. A cellular reporter is not required in such instances because verification of ablation, regeneration and/or the lack of regeneration can be determined by outwardly detectable observations.

In a further aspect, transgenic zebrafish undergoing cellular ablation and subsequent regeneration screening co-express an ablation-promoting gene product and a reporter gene product: In those eases where cellular ablation would not result (or would not be expected to result) in an outwardly detectable phenotype it is necessary to utilize transgenic zebrafish co-expressing an ablation-promoting product and a reporter product for cellular regeneration screens. A cellular reporter is required in such instances because verification of ablation, regeneration and/or the lack of regeneration cannot be determined by outwardly detectable observations.

6b. Screening of Regeneration-competent Transgenic Zebrafish.

As used herein, the term "genetic screen" includes any method of genetic manipulation, most notably "forward" and "reverse" genetic procedures, that facilitates identification of genetic factors which influence a phenotype of interest—the general phenotype of interest considered of this invention being the ability or inability to regenerate specific cells.

As used herein, the term "mutagen" is to be broadly understood as meaning any mutagenic or potentially mutagenic agent, treatment, or event capable of disrupting the genomic structure of an organism: Such agents include but are not limited to, mutagenic chemical compounds (e.g. ENU), exposure to radiation (e.g. x-ray), exposure to an electromagnetic field and viral or transposon insertions.

Transgenic fish expressing an ablation-promoting product, facilitate genetic screens that aim to identify genes, and specific mutations that influence the process of cellular regeneration in vivo. Using such fish it can be determined whether the zebrafish has an inherent capacity for the regeneration of specific cells and tissues as outlined above (section 6a). Fish that demonstrate competence for regeneration of specific cells and tissues (i.e. "regeneration-competent" lines) can be used to identify mutations which compromise the regenerative process as detailed below. Mutant transgenic zebrafish identified in such genetic screens represent animal models for degenerative disorders that provide marked advantages for subsequent pharmacological screens. Due to a comparatively unique amenability to high-volume automated screening among experimental vertebrate model systems, such zebrafish models significantly reduce the time and resources required to identify beneficial therapies.

6b. i) Illustrative Methods of Genetic Screening.

Regarding the general methodology of genetic screens utilizing transgenic zebrafish of this invention; in general, any method of "forward" or "reverse" genetics that when applied to an ablation and subsequent regeneration paradigm can be used to implicate a specific gene as having a role in cellular regeneration is considered applicable to the invention disclosed herein.

Forward genetics, whereby the genome of an organism is randomly mutated, mutant organisms carrying specific mutations are derived and mutant lines are screened fur the phenotype of interest, can be used to identify genetic mutations that impact the inherent regenerative capacity of the zebrafish and thereby implicate specific genes as having a role in cellular regeneration.

Reverse genetics, whereby a particular gene(s) or gene product(s) is functionally disrupted, physically eliminated and/or otherwise compromised in individual organisms (e.g. morpholino "knockdown") or in organisms and their derived progeny (e.g. genetic "knockout"), can also be used to implicate specific genes as having a role in cellular regeneration. Forward genetics therefore emphasizes the biological process first and identifies genes secondarily, reverse genetics emphasizes genes first and tests for effects on a given biological process secondarily.

Zebrafish, like humans, are diploid organisms having two copies of every genetic locus (except sex-linked loci), one from each parent. Therefore, in order to screen for effects of recessive mutations a given mutation must be brought to homozygosity (the m/m state versus the +/+ or +/m state, where in stands for a mutated allele and + stands for the normal—aka wildtype—allele). Mutagenesis screens of zebrafish typically involve crossing mutagenized males to wildtype females. All mutated loci are heterozygous (+/m) in the first filial generation (or, "F1" offspring) of such a cross and therefore all recessive mutations are undetectable. Moreover, in order to bring individual mutations to homozygosity in large numbers—for screening purposes—the F1 generation must first be out crossed to another wildtype parent to create F2 families made up of 50% wildtype (+/+) and 50% heterozygous (+/m) "carrier" siblings. Random incrossing of F2 siblings results in 25% of matings between heterozygous carrier siblings (+/m×+/m). Among F3 progeny from carrier sibling crosses, 25% are homozygous for the, mutation (25%+/+, 50%+/m, and 25% m/m). It is in this population that the effects of recessive mutations can be revealed. Because of the relative inefficiency of this procedure a vast amount of time, space, and energy is required to perform F3 screens. For this reason methods have been developed whereby mutations can be brought to homozygosity in the F2 generation. Moreover, these procedures generally result in the F2 progeny being 50% mutant and 50% wildtype which facilitates the screening process. Genetic screens utilizing transgenic zebrafish for screening purposes have an added level of complexity in that the process is dependent upon the co-propagation of the mutated and transgenic lad. For this reason transgene-expressing progeny are selected when applicable (e.g. by reporter expression) and homozygous transgenic zebrafish are used whenever possible in the induced mutagenesis mating protocols below. However, it should be noted that caveats and practicality may prevent the use of homozygous transgenics in certain instances and therefore alternate procedures are also presented.

In an aspect, a forward genetics based saturation mutagenesis methodology is employed for genetic screens of transgenic zebrafish. Specifically, a mutagenic procedure is applied to zebrafish in such a manner that it is predicted that within the germline of mutagenic founder fish every genetic locus is functionally disrupted at least once. Furthermore, such mutations can be propagated by sexual reproduction in transgenic zebrafish of this invention in order to be brought to the homozygous state in 25% of the transgenic 11 generation of zebrafish derived from a mutagenized founder. More specifically, homozygous transgenic females are mated to mutagenized homozygous transgenic males (tr/tr; +/+×tr/tr; m/m, where m is mutation, tr is transgenic and, + is wildtype) to create F1 progeny that are homozygous at the transgenic locus and heterozygous at a discrete mutated locus (tr/tr +/m). F1 females are outcrossed to homozygous transgenic males (tr/tr; +/m×tr/tr +/+) to create F2 families comprised of siblings that are 50% transgenic carriers and % wildtype transgenics (tr/tr; +/m and tr/tr; +/+). Random matings of F2 siblings results in 25% of matings between transgenic carriers (tr/tr; +/m×tr/tr; +/m). Transgenic carrier crosses result in 25% of the transgenic F3 progeny being homozygous for the mutation (tr/tr; m/m). F3 embryos, larvae, and/or fish from random P2 sibling matings are tested to determine whether homozygous (recessive) mutations impact the process of cellular regeneration (i.e. 25% of fish from an F2 family incross are compromised in their ability to regenerate). In addition, a second generation ("F2") screen can be performed to determine if heterozygous (dominant) mutations can impact the process of cellular regeneration (i.e. 50% of fish from an F1 outcross are compromised in their ability to regenerate).

Optionally—for instance in a case where transgenic lines cannot withstand the mutagenic procedure—homozygous transgenic females are mated to mutagenized wildtype males (tr/tr; +/+×tr/tr; m/m) to create F1 progeny that are heterozygous at both the transgenic and mutated locus (+/tr; +/m). F1 females are outcrossed to homozygous transgenic males (+/tr; +/m×tr/tr; +/+) to create F2 families comprised of siblings that are 50% transgenic carriers arid 50% wildtype transgenics, however, half are heterozygous transgenics and half are homozygous transgenics (25%+/tr +/m, 25% tr/tr; +/m and, 25%+/tr; +/+, 25% tr/tr; +/+). Random matings of F2 siblings results in 25% of matings between transgenic carriers. Transgenic carrier crosses result in 25% of the transgenic F3 progeny being homozygous for the mutation when transgene-expressing progeny are selected since 25% of transgenic carrier crosses will be between heterozygous transgenics it is necessary to specifically select out transgenics at this step. Transgenic P3 embryos, larvae, or fish from random F2 sibling crosses are tested to determine whether homozygous (recessive) mutations impact the process of cellular regeneration (i.e. 25% of fish from an P2 family incross are compromised in their ability to regenerate). Alternatively, a second generation ("F2") screen can be performed to determine if heterozygous (dominant) mutations can impact the process of cellular regeneration (i.e. 50% of fish from an F1 outcross are compromised in their ability to regenerate).

Other variants of transgenic P3 screen mating schemes are also possible (e.g. starting with heterozygous transgenic females and males) the outcome and design of which is a simple matter of classical genetics.

In an aspect, mutations generated by a saturation mutagenesis protocol are propagated in transgenic zebrafish of this invention such that the mutations are brought to homozygosity in the F2 generation of zebrafish derived from a mutagenized founder. This approach utilizes an early pressure or heat shock protocol to generate gynogenetic (also called parthogenetic) diploid organisms from eggs that are fertilized in vitro with UV-inactivated sperm. More specifically, homozygous transgenic females are mated to mutagenized homozygous transgenic males (tr/tr; +/+×tr/tr; m/m) to create F1 progeny that are homozygous at the transgenic locus and heterozygous at the mutated locus (tr/tr; +/m). Eggs are collected from F1 females and fertilized with UV-inactivated sperm, which stimulates the egg to develop without genetic contribution from the sperm. Without intervention such eggs will develop as haploid organisms (50% tr; + and 50% tr; m). If however, the eggs are subjected to pressure within a few minutes of fertilization the meiotic spindle is disrupted and the second cell division of meiosis blocked causing sister chromatids to remain associated in the egg. The eggs go on to develop as diploids having two sets of maternal chromosomes (50% tr/tr; +/+ and 50% tr/tr; m/m). Alternatively, eggs fertilized with UV-inactivated sperm can be subjected to heat shock to block the first mitotic division and thereby develop as diploids. Crossover events during meiosis I cause mutations at the telomeric end of chromosomes to be underrepresented (<50%) in early pressure derived progeny. Because heat shock treatment occurs after meiosis II progeny axe always 50% mutant and 50% wildtype. For this reason heat shock would be the preferred protocol, however, heat shock results in high lethality which compromises the practicality of the approach. Regardless, either approach—or any other protocol resulting in the generation of gynogenetic diploid zebrafish—is considered applicable to the invention disclosed herein.

In an aspect, a reverse genetics based methodology is employed for genetic screens of the transgenic zebrafish. For instance, a chemically modified anti-sense oligomer approach (commonly called, "morpholino"—for the type of chemical modification added to the oligomer) has been shown to work quite effectively in zebrafish (Nasevicius and Ekker, 2000). Morpholinos function by blocking the translation of mRNA into proteins, an effect that has been termed, knockdown. Morpholinos have the advantages of being: i) relatively stable; ii) specific or combinatorial—individual genes can be targeted or more than one gene can be targeted at a time; iii) independently labeled—morpholinos can be conjugated to reporters allowing mosaic analyses of "morphant" and wildtype tissues in a single organism, and iv) fast—morpholinos are injected into fertilized embryos and the effects can be determined over the course of the next 24 to 96 hours. Possible disadvantages include: i) high phenotypic variability; ii) non-specificity—oligos may react with more than one mRNA; iii) limited efficacy—effects generally limited to early development (24 to 96 hours post-fertilization). In general, the morpholino approach—or any other reverse genetic protocol resulting in the specific disruption of a targeted gene or genes—is considered applicable to the invention disclosed herein.

Regarding the composition and utility of the mutagen used to create mutant transgenic fish of this invention; in general any agent or event capable of producing deleterious mutations in the germline of zebrafish is considered applicable to the invention disclosed herein.

In an aspect, the mutagen is applied such that it is predicted that the germline of mutagenized fish contains at least one deleterious mutation at every genetic locus.

In an aspect, a mutagen is employed which facilitates the process of identifying the site of deleterious mutations (e.g. viral or transposon integration).

In an aspect, the mutagen employed promotes single point mutations (e.g. ENU, (Solnica-Krezel et al., 1994).

6b. ii) Method of Identifying Genetic Mutations.

After establishing mutant fish lines that have a regeneration phenotype of interest comes the process of identifying and cloning the affected genes responsible for the phenotype. This process begins by meiotically mapping the mutation to a discrete chromosomal region. Many techniques have been developed for this process in zebrafish, including but not limited to, simple sequence length polymorphisms (SSLPs), restriction fragment length polymorphisms (RFLPs), single nucleotide polymorphisms (SNPs), somatic cell hybrid panels and radiation hybrid panels. Mutants are first meiotically mapped; mutant and wildtype individuals from a mapping cross are typed for well distributed markers across the genome (~20 centimorgan, CM, average spacing) to identify linked regions. The linked region is targeted with additional markers to further limit the critical region—typically 2000 individual meiosis mapping panels are used to achieve ~50 kb resolution. Mapping proceeds by identifying polymorphisms within this region to further delimit the critical interval. Genes are then identified within the critical region and: i) sequenced to identify specific genetic lesions (i.e. mutations); ii) analyzed for their expression pattern during development and within the paradigm of cellular regeneration; iii) disrupted in wildtype fish using morpholino anti-sense knock-down in order to phenocopy the mutation and; iv) tested for cDNA rescue—whereby expression of the wildtype gene is used to rescue the mutant defect—in order to verify the identity of the affected gene in any given mutant strain.

Regarding the methodologies used to identify genetic mutations in zebrafish: in general, any method of detecting, mapping, verifying, cloning, and sequencing genetic mutations in zebrafish is considered applicable to the invention disclosed herein. Preferred are methods which increase the pace at which a given mutation can be identified such as coupled mutagenesis screening and genetic mapping (Rawls et al., 2003).

6b. iii) Ablation-Based Forward Genetic Screening of Regeneration-Competent Transgenic Zebrafish.

A method is provided for creating and identifying mutant fish that have a compromised capacity for cellular regeneration with respect to specific cells or tissues and/or following a modeled injury. Individual mutations are propagated as described above (6b. i) in transgenic F2 and/or transgenic F3 generations derived from a mutagenized founder. Such progeny are screened for any indication of a compromised capacity for cellular regeneration in a predicted percentage of progeny that harbor the genetic mutation: 50% if heterozygous dominant (F2 and P3 generation screens); 50% if homozygous recessive (P2 generation screens only) and; 25% if homozygous recessive (F3 generation screens only), such that they are now impaired and/or unable in their ability to generate cells they were previously competent to regenerate.

A generalized protocol for forward genetics based regeneration. screening in transgenic zebrafish of this invention includes: 1) Transgenic expression of an ablation-promoting moiety—or co-expressing an ablation promoting and a reporter gene product—in a cell type specified by discrete regulatory regions which are uniquely active during the specification, and/or maturation, and/or at maturity of the given cell, cell type, or tissue; 2) Generation of transgenic lines stably expressing a cell and/or tissue specific ablation-promoting moiety; 3) Generation of individual mutant transgenic lines by mutagenesis as outlined above (6b. i); 4) Testing individual mutant transgenic fish and/or mutant transgenic fish lines for their regenerative capacity according to the generalized protocol for targeted cellular ablation and regeneration screening above (6a. i) but with the following modification: Transgenic mutant fish and/or transgenic mutant lines are distributed such that they are presented individually or in defined groups to the device(s) used for verifying cellular ablation and/or detecting cellular regeneration—for instance, by arraying in multi-well formats or by virtue of the design of the device (e.g. the COPAS fluorescence sorter from Union Biometrica); 5) Introduction of a pro-drug into embryonic, larval, or adult mutagenized transgenic zebrafish such that the pro-drug is presented to an appropriate pro-drug converting moiety produced by transgene expressing cells; 6) Conversion of the pro-drug to its cytotoxic form by action of the pro-drug converting moiety; 7) Specific ablation of transgene expressing cells (or regional ablation of transgene expressing and nearby cells in the case of the modeled injury), when such cells are exposed to a sufficient concentration of the cytotoxic drag produced upon pro-drug conversion; 8) Verification of cellular ablation by detection of an outwardly visible cell loss, a detectable loss of reporter product signal, an outwardly or otherwise detectable phenotypic change, and/or any other indications of an induced cellular loss; 9) Subsequent removal of the pro-drug and/or its cytotoxic derivative(s) from the embryonic, larval, or adult transgenic zebrafish; 10) An initial assessment of any evidence of change in the capacity for cellular regeneration by observation of outwardly detectable regenerating cells, by the return of reporter product signal, by the remission of a phenotypic change induced upon cellular ablation and/or any other indications of repairing the induced cellular loss in a predicted percentage (as described above) of treated fish that would correspond to those fish harboring the genetic mutation being now unable to regenerate cells they were previously competent to regenerate; 11) Verification of a compromised capacity for cellular regeneration in those fish harboring the mutation by a failure to detect the return of morphological, physiological, cellular, molecular, and/or any other functional hallmarks that are definitively associated with the cell type that was ablated; 12) Identification of mutated transgenic zebrafish as degenerative disease/condition models with respect to the ablated cell(s), cell type(s), and/or tissue(s); 13) Propagating the genetic mutation through germline transmission for the purposes of mapping, cloning, and sequencing the precise genetic alteration responsible for the change in regenerative capacity, and; 14) Identification of the gene mutated (and the precise) genetic mutation as one impacting the process of cellular regeneration and/or cell type specific regeneration in a vertebrate organism, whereas the mutation is causally linked to a change in the regenerative capacity of transgenic zebrafish, such that regeneration-competent transgenic zebrafish are now deficient to regenerate cells they were previously competent to regenerate.

In an aspect, the method for ablation-based forward genetic screening of regeneration-competent transgenic zebrafish (6b. iii, above) is equivalently applicable to screening regeneration-deficient transgenic zebrafish for a change in their regenerative capacity such that those fish harboring the genetic mutation are now able to regenerate cells they were previously deficient to regenerate.

If desired, subsequent regeneration-based mutagenesis assays can be conducted in phases of primary, secondary, tertiary, etc., which become progressively more detailed in terms of defining the degree to which regeneration is compromised. In addition, high volume (aka, high-throughput) methods can be applied during screening procedures to increase screening efficiency. For automated screening, fish embryos, larvae and/or adults are arrayed in multi-well formats or passed sequentially through optical devices capable of sensing the reporter gene product and/or a detectable byproduct of reporter gene product activity. In this way, it is possible to obtain large numbers of samples per condition and use statistical analyses to identify conditions wherein the regenerative capacity of the zebrafish is subtly altered. Moreover, because automation allows larger sample sizes to be analyzed the number of mutations that can be meaningfully assessed within a given amount of time necessarily increases. The ability to automate aspects of all screening processes described herein will greatly reduce the time and resources required to get from disease model to therapeutic target.

6c. Pharmacological Screening of Regeneration-Deficient Zebrafish.

As used herein the term "pharmacological screen" includes any method of testing the effects of an exogenous factor on the phenotype and/or phenomenon of interest in a model organism—the general phenotype of interest of this invention being the ability or inability to regenerate specific cells in zebrafish.

Zebrafish are eminently suited to high-throughput small molecule screening (Patton and Zon, 2001; Peterson et al., 2000). In that regard, large numbers of eggs can be generated at a single time by group matings (and/or several individual mating pairs) providing sizeable pools of genotypically equivalent test organisms. As embryos, larvae, and young adults they can be arrayed in multi-well trays and screened using high-throughput approaches—for instance, robotic arm delivery of small molecules—to determine the effects of any chemical or reagent presented over the course of several days and at a range of concentrations. In addition, combinatorial chemistry can be brought to bear to optimize the effectiveness of any lead compounds by subtly varying their chemical composition in a reiterative screening approach. Manual screens have shown that the number of compounds that can be screened by an individual is limited to approximately 400 compounds per day (Peterson et al., 2000). Reporter genes allow the screening process to be automated thus increasing the number of compounds screened per day dramatically—limited essentially only by the number of eggs that can be produced in a given day. In order to facilitate detection of reporter elements the transparency of the fish can be maintained pharmacologically (using a final concentration of 0.003% 1-phenyl-2-thiourea, PTU) or genetically (e.g. albino, transparent, and roy orbison mutants).

6c i) Method of Pharmacological Screening.

A method is provided for identifying small molecule compounds that promote cellular regeneration in regeneration-deficient transgenic fish with respect to specific cells or tissues and/or following a modeled injury. Deficiency for regeneration can be the result of specific mutations or due to an inherent inability to regenerate cells.

In the case of an inherent ability to regenerate cells, transgenic fish and their progeny can be used directly. In the case where a mutation has resulted in a compromised regenerative capacity, individual mutations are propagated as described above (6b. i) such that transgenic F2 and/or transgenic F3 generations derived from a mutagenized founder represent some percentage of heterozygous (dominant) and/or homozygous (recessive) mutated alleles, Progeny are screened in the presence of small molecule compounds for any indication of an increased capacity for cellular regeneration in that percentage of offspring that harbor the genetic mutation such that they are now able to generate cells they were previously deficient to regenerate.

A generalized protocol for pharmacological screening of regeneration-deficient transgenic zebrafish of this invention includes: 1) Transgenic expression of an ablation-promoting moiety—or co-expressing an ablation promoting and a reporter gene product—in a cell type specified by discrete regulatory regions which are uniquely active during the specification, and/or maturation, and/or at maturity of the given cell, cell type, or tissue; 2) Generation of transgenic lines stably expressing a cell and/or tissue specific ablation-promoting moiety; 3) Determination of the inherent regenerative capacity of individual transgenic lines with respect to specific cells or tissues and/or following a modeled injury; 4) Generation of individual regeneration—deficient mutant transgenic lines as outlined above (6b. i) in those transgenic lines that have an inherent regenerative capacity; 5) Testing individual small molecule compounds for the ability to promote regeneration in regeneration-deficient transgenic fish and/or mutant transgenic fish lines by arraying these fish such that they are presented individually or in defined groups to the device(s) used for verifying cellular ablation and/or detecting cellular regeneration—for instance, by arraying in multi-well formats or by virtue of the design of the device (e.g. the COPAS fluorescence sorter from Union Biometrica); 6) Introduction (as by manual addition of the pro-drug into a solution containing transgenic zebrafish) of a pro-drug into embryonic, larval, or adult regeneration-deficient transgenic zebrafish such that the pro-drug is presented to an appropriate pro-drug converting moiety produced by transgene expressing cells; 7) Conversion of the pro-drug to its cytotoxic form by action of the pro-drug converting moiety; 8) Specific ablation of transgene expressing cells (or regional ablation of transgene expressing and nearby cells in the case of the modeled injury), when such cells axe exposed to a sufficient concentration of the cytotoxic drug produced upon pro-drug conversion; 9) Verification of cellular ablation by detection of an outwardly visible cell loss, a detectable loss of reporter product signal, an outwardly or otherwise detectable phenotypic change, and/or any other indications of an induced cellular loss; 10) Subsequent removal of the pro-drug and/or its cytotoxic derivative(s) from the embryonic, larval, or adult transgenic zebrafish; 11) Presentation of effectively solubilized small molecule compounds or control solutions to individual fish or sets of fish such that adequate numbers of treated and untreated fish are maintained for statistical comparisons; 12) An initial assessment of any evidence of change in the capacity for cellular regeneration in treated fish by observation of outwardly detectable regenerating cells, by the return of reporter product signal, by the remission of a phenotypic change induced upon cellular ablation and/or any other indications of repairing the induced cellular loss, and a comparison of these effects to untreated control fish; 13) Verification of cellular regeneration by the detection of morphological, physiological, cellular, molecular, and/or any other functional hallmarks that are definitively associated with the cell type that was ablated, in cells that were generated following the ablation of the target cells; 14) Identification of compounds capable of promoting a change in the regenerative capacity of transgenic zebrafish such that regeneration-deficient transgenic zebrafish are now competent to regenerate cells they were previously deficient to regenerate, as target compounds capable of promoting cellular regeneration and/or cell type specific regeneration in a vertebrate organism.

In an aspect, the method for pharmacological screening of regeneration-deficient transgenic zebrafish (6c., above) is equivalently applicable to screening regeneration-competent transgenic zebrafish for a change in their regenerative capacity such that regeneration-competent transgenic zebrafish are now deficient regenerate cells they were previously competent to regenerate. In this instance, target compounds would be identified that promote cellular degeneration and/or cell specific degeneration in a vertebrate organism.

6c ii) Method of Optimizing Regeneration-Promoting Compounds.

Subsequent regeneration-based pharmacological assays can be conducted in phases of primary, secondary, tertiary, etc., which become progressively more detailed in terms of optimization of lead compound treatments which show evidence of promoting cellular regeneration with regard to effective dose concentration, chemical composition and in terms of the degree to which "replacement" cell(s) display hallmarks of the ablated cell(s), and/or tissue(s). For example, compounds identified in initial screens can be modified by combinatorial chemistry methodologies in order to define more efficacious treatments.

If desired, existing extensive small molecule libraries can be made for initial screening efforts of the novel methods herein. High volume methods can be applied in all phases to increase screening efficiency. The ability to automate aspects of the screening process will greatly reduce the time and resources required to go from disease model to therapeutic target.

The invention disclosed herein comprises a unique methodology for elucidating molecular regulators and genetic circuits of cellular regeneration in zebrafish. Moreover, our discovery provides a versatile and highly efficient approach to discovering regenerative therapies for degenerative conditions.

Our discovery comprises the creation and utilization of novel transgenic zebrafish that express an ablation-promoting gene product, or co-express an ablation-promoting gene product and a reporter gene product in specific cells, cell types, or tissues. Mutations are propagated in such fish to identify genes which function in the pathway(s) of cellular regeneration. Molecular compounds are introduced into such fish, and in mutant strains of such fish, to identify agents that can promote the process of cellular regeneration.

EXAMPLES

The examples following are meant to be an illustrative application of the invention disclosed herein and are in no way meant to be limiting the scope.

This example was useful for demonstrating functionality of an established pro-drug conversion system in transgenic zebrafish, whereby those cells expressing a pro-drug converting moiety (e.g. nitroreductase) coupled with a reporter protein (e.g. CFP) were selectively ablated upon contact with a pro-drug defined as promoting targeted ablation (e.g. metronidazole).

In order to determine the efficacy of nitroreductase-based pro-drug conversion and subsequent cellular ablation in transient transgenic zebrafish the following experiment was performed: Male and female zebrafish from a 'transparent' strain (e.g., harboring the roy mutation) were allowed to mate over egg collection chambers at light onset. Fertilized eggs were collected every 15 minutes and placed in petri dishes containing embryo medium (0.3× Danieau's solution containing 100 units/ml penicillin and 100 µg/ml streptomycin). Eggs were dispensed into a silicone chambers and oriented such that the cell side was facing up. For injections, DNA plasmids were diluted into 1× Danieau's solution to a final concentration of 10 ng/µl. DNA plasmids used for this experiment included: 1) An alpha-1-tubulin promoter driving expression of a Gal4/VP 16 "driver" protein (α-1-tub::Gal4/VP16); 2) A UAS regulated red control fluorescent reporter protein (UAS::DsRed) and; 3) A UAS regulated cyan fluorescent reporter protein (unc-CFP) fused to nitroreductase (UAS::unc-CFP-Nitro, see FIG. 2 and FIG. 3). Single cell eggs were injected with 25-100 µL of the injection solution using a Picospritzer II (General Valve Corp.) to control air pressure and duration of the injection pulse, and thereby the injection volume. Following injection eggs were rinsed into a petri dish containing embryo medium and incubated at 28.5 C. PTU (1-phenyl-2-thiourea) at 0.003% was added to the embryo medium at approximately 15 hours post-fertilization (hpf) to inhibit residual pigmentation evident in the roy mutant strain. At 28 hpf, injected embryos were screened for equivalent expression of the DsRed reporter (control cells) and the unc-CFP-Nitro ablation/reporter (targeted cells) using standard fluorescence microscopy. Selected embryos were returned to the incubator and allowed to develop normally until 62 hpf. Pre-treatment images were collected for each embryo at 62 hpf using confocal microscopy to detail reporter expression patterns evident in the head region essentially as described in Kay et al., 2004. Briefly, embryos were anesthetized in embryo medium containing 0.003% PTU and 0.02% tricaine, immersed in 0.5% low melt agarose (maintained at 40° C.) containing equivalent amounts of PRU and tricaine, and mounted on glass slides with the left side facing up. Following confocal imaging, embryos were individually released and placed in separate wells of 24-well tissue culture dishes containing 250 µl of embryos medium. Embryos were randomly divided into untreated control and pro-drug (metronidazole) treated groups. 250 µl of embryo medium (controls) or embryo medium containing metronidazole (treated) was then added to each well. A 50 mM stock of metronidazole made up in embryo medium was diluted to 2× concentrations prior to addition to treated wells. Final concentrations of metronidazole tested were 10 mM, 5 mM, and 2.5 mM. Embryos were then returned to the incubator and maintained at 28.5° C. until 118 hpf at which time each embryo was anesthetized, mounted, and imaged as above. All exposure and laser intensity settings used for pre-treatment imaging were utilized again in post-treatment imaging in order to normalize detection of the DsRed control and unc-CFP-Nitro reporters. Representative images from this experiment are shown in FIG. 3. The data clearly demonstrate the selective elimination of unc-CFP-Nitro expressing cells in embryos treated with metronidazole. In contrast, untreated embryos maintain robust expression of both control (DsRed) and nitroreductase linked (unc-CFP-Nitro) reporters. Note that the reduced level of DsRed expression seen in the metronidazole treated embryo is due to co-expression of DsRed and unc-CFP-Nitro in many of the cells. In addition, the persistent expression of unc-CFP-Nitro seen in the lens of the metronidazole treated embryo is expected as cells in the lens are no longer metabolically active at this stage and thereby cannot convert metronidazole into its cytotoxic form.

This example is useful to demonstrate the methods of creating novel transgenic zebrafish expressing ablation-promoting products, or co-expressing ablation-promoting products and reporter products, in specific cells or cell types and the methods of utilizing such fish for the useful purposes disclosed herein.

A. Transgenic Zebrafish.

Procedure for producing novel transgenic zebrafish co-expressing an ablation-promoting gene product and a fluorescent reporter gene product:

All zebrafish are maintained under optimal environmental conditions in a recirculating aquaculture system under a 14/10 subjective light/dark cycle. For maximum egg production zebrafish are fed a regimen of enriched flake food and live brine shrimp three times daily. Zebrafish are naturally induced to mate at light onset. Accordingly, eggs are collected from mating chambers in the subjective morning and placed in petri dishes containing 0.3× Danieau's solution with penicillin and streptomycin (embryo medium). One cell stage eggs are immediately sorted out and oriented cell side up in injection chambers. Transgenic DNA constructs suspended in a 1× concentration of Danieau's solution are microinjected into one cell stage embryos using a Picospritzer II (General Valve Corp.) to control injection volume and a Narishige micromanipulator (model MN-is 1) to control the injection capillary. All injected embryos are placed back into petri dishes containing 0.3× Danieau's solution with penicillin and streptomycin and maintained at 28.5 C. After such time that is appropriate for the transgenic construct to express, injected embryos are observed under fluorescent microscopy and those displaying fluorescence are selected out and raised to sexual maturity. At sexual maturity these fish are individually mated and their progeny are screened under fluorescent microscopy for expression of the fluorescent reporter. Up to 300 embryos/larvae are screened from individual matings before fish failing to produce any fluorescent offspring are euthanized by immersion in 20×MS-222 solution (aka, tricaine at 0.1%). Fish producing fluorescent offspring are "transgenic founders" and those offspring that are fluorescent represent the first generation of individual transgenic lines. Individual transgenic lines can vary in terms of the expression pattern of the transgene product. Therefore, fluorescent progeny from each individual transgenic line are further screened for expression patterns of interest. When a given line displays cell and/or tissue specific fluorescent expression patterns (or that express in a general pattern of interest) the fluorescent progeny are selected out, raised to maturity, and maintained as individual transgenic lines.

In the case where novel transgenic zebrafish expressing only an ablation-promoting gene product are produced the following modifications are necessary for detecting transgenesis: 1) All injected fish are raised to sexual maturity and fin clippings are screened by PCR for the presence of the transgene; 2) Transgene containing fish are individually mated and eggs are pooled and screened by PCR for the presence of the transgene; 3) Those fish identified as founders are individually mated and all offspring are raised to sexual maturity; 4) Fin clippings from offspring are then screened by PCR for the presence of the transgene using primers that anneal specifically detect the transgene; 5) Offspring containing the transgene are selected out and maintained as transgenic lines. To determine whether the transgene product is expressed in a pattern of interest in a given transgenic line, individual lines are mated and embryos/larvae screened by immunohistochemistry. Those that display cell or tissue specific expression patterns (or that express in a general pattern of interest) are maintained as individual transgenic lines.

In a specific example, a DNA sequence encoding a GFP-Nitroreductase fusion protein (the transgene product) is inserted into the coding sequence of the ChAT (choline acetyltransferase) locus of Takifugu rubripes. This transgenic construct is introduced into single-cell zebrafish embryos to produce transgenic zebrafish expressing the transgene product in cholinergic neurons of the zebrafish.

A2. Transgene Product—XFP-Nitroreductase.

Fluorescent proteins (collectively termed here, XFPs—cyan, green, and yellow being CFP, GFP, and YFP etc.), such as the green fluorescent protein (GFP) from the jellyfish *Aequorea victoria*, have become popular tools for non-invasive detection of cells in vivo. Such proteins emit visible light when "excited" by lower frequencies of light and are thereby detectable without the need of any co-factors other than a light source (e.g. a laser) and a fluorescent detector (e.g. a microscope) outfitted with appropriate filter sets that allow excitation light frequencies to be discretely presented to the fluorescent protein and emission light frequencies to be separably detected (Chalfie, 1995; Chalfie et al., 1994; Tsien and Miyawaki, 1998). In addition, many variants of GFP as well as fluorescent proteins from other species have been identified which have increased fluorescence properties, alternative excitation and emission properties, and/or other properties of general use such as a destabilized version that facilitates studies of promoter expression patterns (Gross et al., 2000; Heim and Tsien, 1996; Tsien, 1999; Zhang et al., 2002). The use of GFP in zebrafish has been particularly useful for the studying aspects of zebrafish development due to the fact that zebrafish embryos are transparent and therefore easily visualized.

Pro-drug conversion systems, such as bacterial nitroreductase, have been developed as tools for targeted cellular ablation typically with regard to methods for specifically eliminating cancer cells (Bagshawe et al., 1999; Denny, 2001; Xu and McLeod, 2001). To date, their use as tools for cellular ablation as a general paradigm have been limited. However, examples in mice and mouse stern cells have been reported (Fareed and Moolten, 2002; Felmer et al., 2002). Of particular importance here, a fusion protein between GFP and nitroreductase was shown to be functional for both fluorescent detection and selective ablation in cell culture (Medico et al., 2001).

A3. Transgenic Construct

One method for co-expression of both a reporter and a prodrug conversion enzyme is to create a fusion protein containing both activities. This fusion protein creates the most tightly coupled expression of the two activities since a single polypeptide chain is translated and the two normally separate peptides are covalently linked. In an aspect the Nitroreductase gene from *E. coli* is cloned and fused a fluorescent reporter protein. Enzymatic activity from Nitroreductase allows cleavage of the pro-drugs CB1954 and metronidazole promoting ablation while the fluorescent reporter protein allows detection of expressing cells by monitoring with a standard fluorescent microscope setup.

The Nitroreductase coding region was amplified by the Polymerase Chain Reaction (PCR), Two primers designed to hybridize to sequence flanking the gene and containing convenient restriction sites were used. The primer designed to hybridize upstream of nitroreductase contained the sequence: 5'-ATGCTCGAGCCATGGATATCATTTCTGTCGCCTT A-3' (SEQ ID NO:1). This upstream primer contains Xho I and Nco I restriction sites and optimizes the initiation site for eukaryotic translation. The primer designed to hybridize downstream of the nitroreductase coding region contains an introduced BamH I restriction site and has the following sequence: 5'-GGGGATCCGATCGATCTCAATACCCGCT-AAATA-3' (SEQ ID NO:2). Amplification of the nitroreductase coding region was performed using *E. coli* genomic DNA in 50 gl using the following concentrations of reagents: Primers, 1.0 μm; dNTP's 200 μm each; Klentaq LA (Sigma, St. Louis Mo.) 1.0 μl; 1× enzyme buffer. The amplification was accomplished in a thermal cycler programmed to heat the sample to 94 C for 1 min followed by 25 cycles of 94 C for 15 sec; 55 C for 15 sec and 72 C for 4 min. Following the amplification the product was checked by agarose gel electrophoresis and a band of the expected size (~700 bp) was detected. The expected sequence of the product of this reaction is shown in the sequence listing attached.

To clone the resultant product nitroreductase was first fused to the enhanced CFP coding sequence in pECFP-C1 (Clontech, Palo Alto Calif.). The PCR product digested with BamH I and Xho I and gel purified. pECEP-C1 vector was prepared by digesting with Xho I and BamH I and gel purified. Vector and insert were ligated and the resulting transformants were screened for the insertion of the nitroreductase coding region and the loss of most of the CMV promoter of pECFP-C1. The resulting plasmid is pECFP-Nitro. A map drawing of the contents of this plasmid is found in FIG. 4. This plasmid vector contains a pUC plasmid origin of replication an f1 origin of replication for producing single stranded DNA for sequencing as well as a dual *E. coli*/Eukaryotic kanamycin/neomycin selection cassette. These components are used in this plasmid for propagation and maintenance in *E. coli* and mammalian tissue culture but are not necessary for gene expression in the fish. In addition the plasmid Cytomegalovirus promoter (CMV), and a SV40 polyadenylation signal flank the protein coding region and can be used for regulatory sequences for expression in fish cells. The CMV promoter, however, produces lower levels of expression in zebrafish.

To create a plasmid that could be used with the Gal4VP16 amplification system the pECFP-Nitro coding sequence was inserted into the plasmid UAS-uncCFP. Both plasmids were with Afl II and Age I. The vector sequences of UAS-uncCFP and the coding sequences of pECFP-Nitro were purified by agarose gel electrophoresis, ligated and transformed into *E. coli*. Resulting colonies were screen for insertion of the ECFP-Nitro fusion sequences. A drawing of the resulting plasmid, UAS-uncCFP-Nitro, is found in FIG. 5. This plasmid replaces the CMV promoter with 14 repeats of the fused to a Carp β-actin core promoter (14×UAS, Koster and Fraser 2001). In addition a 188 amino acid localization tag from the unc-76 protein is fused to the N-terminus of ECFP-Nitro. This sequence localizes proteins preferentially to neurites allowing enhanced monitering of neurons.

To increase the level of protein expression obtained by transient transgenesis a Gal4/VP16— UAS amplification system can be employed (Koster and Fraser, 2001). This system has been shown to promote high levels of persistent protein expression in zebrafish after injection of the system into fertilized eggs. This system is also modular; regulatory & promoter sequences drive the expression of a Gal4/VP16 fusion protein (Gal4 driver) that is capable of binding to Gal4 Upstream Activating Sequences (UAS reporter) placed upstream of protein encoding sequences that can be on the same or a separate DNA plasmid. Thus, a single (Gal4 driver can be used to drive several UAS reporters when all elements are co-linked and/or co-injected.

A4. Microinjection of Transgenic Construct

Large numbers of single cell fish eggs are collected at light onset from mating pairs and/or group matings and maintained in embryo medium. Eggs ale arrayed in injection chambers with the cell side facing up. The transgenic construct is diluted into 1× Danieau's solution to a concentration that is empirically defined as one that promotes maximal survival and maximal transgene expression when injected at high volume (1 to 1.5 nl). Single cells are injected using a Picospritzer II (General Valve Corp.) to control air pressure and duration of the injection pulse—for large volume injections a long low pressure injection is preferred. After all eggs in a given chamber have been injected the eggs are transferred into a 100 mm petri dish containing embryo medium and maintained at 28.5 C. Dead embryos are removed approximately 12 hours after the injection and the remaining eggs incubated overnight or until such time as is appropriate to screen for transgene expression. In those cases where transparency of the developing larvae is desired PTU (0.003% 1-phenyl-2-thiourea) may be added at approximately 15 hours post-fertilization (hpf) to inhibit pigmentation.

A5. Detection of Transgenic Expression in Potential Founders

Approximately 30 hours after microinjection embryos are screened for expression of the reporter gene. In the case of ChAT::XFP-Nitro for instance, fluorescence microscopy is used to detect the presence of the fluorescent reporter. In the case where no reporter is used the injected fish are allowed to develop to adulthood and tail DNA samples taken for PCR analysis. The tail clipping is digested in DNA extraction buffer and prepared for PCR as described previously (Talbot and Schier, 1999). Oligos generated against the transgene sequence are used to amplify trans gene sequence from genomic tail digests. Those larvae expressing detectable levels of the transgene (reporter) or containing detectable levels of the transgene (PCR) are selected out and propagated to adulthood as potential transgenic founders, non-expressing larvae are euthanized in a 20× tricaine solution (0.1%).

A6. Detection of Germline Transmission of Transgene

Once potential transgcnie founders reach sexual maturity (approximately three months) they are mated as groups or as individual mating pairs in order to determine whether they can produce transgenic offspring. Eggs are collected from such matings transferred into 100 mm petri dishes and maintained in embryo medium at 28.5° C. until such time as is appropriate for detecting transgene expression. For instance, in the case of a transgenic fluorescent reporter fluorescence microscopy is used to detect the presence of the fluorescent reporter. Those fish producing transgene expressing offspring are maintained as transgenic founders. Transgene expressing progeny are maintained as F1 generation transgenics, given a transgenic allele designation, and propagated as an individual transgenic line. In the case where no reporter is used PCR analysis is required to assess germline transmission essentially as described above except that entire clutches of eggs can be screened in order to initially define a transgenic founder. In addition, in the case where the transgenic construct comprises a co-expression system of an ablation-promoting moiety and a reporter moiety an ablation assay (see below) and/or PCR analysis is used to verify co-expression of the reporter and ablation components.

B. General Ablation Protocol

To facilitate near simultaneous cellular ablation in large numbers of organisms, embryos and/or larvae are typically arrayed in a multi-well format and maintained in embryo medium. The first step in the ablation protocol establishes an effective dosage of pro-drug that is specific for the desired outcome—e.g. targeted or regional ablation. Each transgenic line requires an empirical assessment of the efficacy of any specific pro-drug utilized. Fish can be presented with a range of concentrations of pro-drug (and/or solubilizing agent, if necessary) in order to define the appropriate level for a given application. In some instances the outcome is influenced by inherent properties of the pro-drug employed, for instance the pro-drug CR 1954 promotes regional ablation while metronidazole promotes targeted ablation upon conversion by nitroreductase. Such assays also serve as general toxicity profiles in the event the pro-drug has deleterious non-specific effects. Once the effective dose is determined a concentrated stock solution (2× to 100×) of pro-drug is made in embryo medium, with the addition of a solubilizing agent such as dimethylsulfoxide (DMSO) if necessary. To initiate ablation the stock solution is added to each well such that the final concentration is brought to IX, controls wells receive an equivalent amount of embryo medium (±solubilizing agent). Stock solutions can be added manually or by automated robotic arm delivery. After the pro-drug is administered the fish are closely observed to determine the timecourse of ablation. Manual visual inspection, using fluorescent microscopy to detect a loss in fluorescent reporter signal or standard microscopy to detect an outwardly verifiable cellular loss, can be used for this purpose. Alternatively, automated fluorescent detector devices can be employed to process large numbers of fluorescent reporter expressing transgenic organisms in a short period of time.

B1. Targeted Ablation

For targeted ablations every effort must be made to ensure that only those cell types expressing an ablation-promoting transgene are eliminated upon treatment. One way to accomplish this goal, specifically with regards to this invention, is through the selection of the specific pro-drug utilized. For instance, the pro-drug metronidazole as a substrate for nitroreductase—due to nitroreductase requiring NAD(P)H (Knox et al., 1988) for conversion to a cytotoxic form and because the cytotoxic form is membrane impermeable—has been defined as a pro-drug which specifically promotes targeted cellular ablation (Medico et al., 2001). In addition, metronidazole has been previously shown to have no general toxicity when administered to zebrafish (Lanzky and Halling-Sorensen, 1997).

In order to verify the specificity of any pro-drug/enzyme combination a modular expression system that facilitates the visualization of ablation targeted and control cells in a single fish can be used. The expression of fluorescent protein-enzyme fusions in targeted cells and fluorescent proteins alone in control cells can be co-regulated in a mosaic fashion by co-injection with a common regulatory element. By co-injecting two different colored UAS constructs (e.g. UAS::YFP and UAS::CFP-Nitro) together with another construct which expresses the UAS DNA binding/activating factors (e.g. alpha1-tubulin::Gal4/VP16, Koster and Fraser, 2001) transient transgenic fish with clones of cells expressing either YFP alone, CEP-Nitro alone, or both constructs together are created (FIG. 2). Clones of YFP expressing cells that are near clones of CFP-Nitro expressing cells can be used to demonstrate targeted and/or regional ablation. In the targeted ablation case when all three types of clones are found in close proximity the administration of pro-drug is shown to selectively ablate only the cyan-positive cells (CFP-Nitro and YFP/CFP-Nitro expressing clones) while leaving the yellow cells intact (YFP expressing only). In the regional ablation case when all three types of clones are found in close proximity the administration of pro-drug is shown to ablate both cyan-positive cells (CFP-Nitro and YFP/CFP-Nitro expressing clones) and neighboring yellow cells (YFP expressing only). Using a variation of this approach—whereby stable transgenic lines co-expressing an ablation promoting moiety and a reporter moiety are injected with a different colored control reporter—it is possible to empirically define an optimal concentration of pro-drug for targeted specificity in each individual transgenic line. In addition, immunocytochemical or histochemical techniques can be used to demonstrate the specificity of cellular ablation. For instance antibodies against the targeted population and a nearby control population could be used to show that only the targeted cell type is eliminated following pro-drug treatment. Once a targeted concentration of pro-drug is determined, large-scale screening can commence essentially as described above (B. General Ablation protocol).

B2. Regional Ablation

For regional ablations the concept is to model a general injury that leads to a degenerative state of the tissue involved (e.g. spinal cord injury). Regional ablation utilizing a pro-drug conversion system has been developed as a means of ablating cancer cells (Bagshawe et al., 1999; Denny, 2001; Xu and McLeod, 2001), the general phenomenon of non-specific ablation being termed the "bystander effect" (Bridgewater et al., 1997). One way to accomplish this goal, specifically with regards to this invention, is through the selection of the specific pro-drug utilized. The pro-drug CE 1954 as a substrate for nitroreductase—due to the permeability of the cytotoxic metabolite—has been shown to specifically promote the bystander effect (Bridgewater et al., 1997; Wilson et al., 2002).

In order to determine an effective regional ablation-promoting treatment for any pro-drug/enzyme combination we can again utilize a modular expression system that facilitates the visualization of targeted and control cells in a single fish as discussed in the section above, In this case however, a concentration of pro-drug would be selected that succeeds in ablating not only enzyme-expressing cells but also nearby controls—i.e. yellow clones of YFP expressing cells that are near cyan clones of CFP-Nitro expressing cells are also eliminated upon treatment. Using a variation of this approach—whereby stable transgenic lines co-expressing an ablation promoting moiety and a reporter moiety are injected with a different colored reporter it is possible to empirically define an optimal concentration of pro-drug for regional ablation in each individual transgenic line. In addition, non-specificity can be verified using immunocytochemical or histochemical techniques to demonstrate regional ablation. For instance antibodies against the targeted population and a nearby control population could be used to show that the targeted cell(s) and nearby neighbors are co-ablated following pro-drug treatment. Once a concentration of pro-drug is determined to be effective for the extent of ablation desired large-scale screening can commence essentially as described above (General Ablation protocol).

B3. Inherent Regenerative Capacity Screen.

Transgenic zebrafish expressing an ablation-promoting moiety facilitate tests of the inherent capacity of zebrafish to regenerate a particular cell, cell type, tissue and/or following a modeled injury. Ablation protocols will be implemented as outlined above according to the type of ablation desired. After sufficient time for successful ablation the pro-drug and cytotoxic derivatives are removed by replacing embryo medium with fresh media. Ablation is verified using techniques appropriate for the cell or tissue type ablated and/or the reporter protein utilized; fluorescent microscopy or equivalent detection techniques for fluorescent reporters and standard microscopy in cases where an outwardly detectable loss and/or phenotype is induced upon ablation. Fish are monitored over the course of the next few days to weeks in order to ascertain the degree to which ablated cells are regenerated. Specific transgenic fish lines are thereby determined to be regeneration-competent or regeneration-deficient with regards to the specific cells or tissues ablated and/or the injury modeled.

C. Genetic Screening.

Transgenic fish that have been determined to be regeneration-competent, with regards to specific cells or tissues and/or a modeled injury, will be subjected to random mutagenesis in order to define mutations which compromise the regenerative response to cell loss. Zebrafish have been established as a vertebrate genetic model system amenable to mutagenic analysis (Driever et al., 1994; (Grunewald and Streisinger, 1992; Mullins et al., 1994; Mullins and Nusslein-Volhard, 1993), and several major forward genetics screens have proven the value of this approach (Amsterdam et al., 1999; Brockerhoff et al., 1995; Driever et al, 1996; Haffter et al., 1996). Transgenic zebrafish facilitate such screens by promoting facile detection of the characteristic or cell type of interest (Hamaoka et al., 2002; Langenau et al., 2003). The invention disclosed herein provides a means to genetically dissect the process of cellular regeneration in terms of factors specific for particular cell types and universal factors required for regeneration in general.

The primary value of such screens comes from the identification of mutations—and thereby genes—that impact the characteristic of interest. In those cases where a given disease or disorder can be modeled it is possible to determine potential causal genetic links to the disease. Several methods have been developed to facilitate the identification of mutant genes in zebrafish. In order to speed the pace at which mutations of interest are mapped and cloned a coupled mutagenesis and genetic mapping protocol has been developed utilizing haplotype inbred lines (Rawls et al., 2003). Using this approach, mutations can be mapped shortly after the genetic screening process is complete.

Genetic screens are conducted as described in the sections above and/or according to current or previously published protocols. Early pressure screens are favored as this approach produces homozygous mutants one generation earlier than standard breeding markedly reducing the amount of time and space required (Beattie et al., 1999). Briefly, adult male zebrafish are mutagenized with ENU to promote single point mutations (Solnica-Krezel et al., 1994). Mutagenized males are bred with females and clutches of eggs from individual F1 females are collected and split into two pools. One pool is used for the screening process, the other is reserved for genetic mapping in the event a mutation of interest is identified (Rawls et al., 2003). Individual F1 females are raised to sexual maturity whereupon eggs are collected and fertilized in vitro with UV irradiated sperm. Eggs are subjected to early pressure in order to inhibit meiosis II, thereby producing gynogenetic diploid organisms (Streisinger et al., 1981). At an appropriate age (generally within three days) larval fish are screened for transgene expression. Around 50% will be transgenic and a subset of transgenics (roughly 50% in the absence of chiasmatic interference) will be homozygous mutants. Families of transgenic F2 siblings are subjected to the appropriate ablation protocol for the degenerative condition being modeled and screened for some percentage of siblings (the percentage that is homozygous mutant) to display an inability to regenerate. Mapping of the mutation will commence when regeneration-deficient mutant fish have been verified for a given family. Individual mutations are propagated by standard breeding of the F1 founder and defined F2 mutants. The mutation will be isolated, sequenced, and verified essentially as described above and/or according to current or previously published protocols. In an effort to show conserved function at the molecular level, cDNA rescue of the mutation can be attempted with paralogs isolated from other species. For instance, if the human paralog can rescue the mutation then it follows that the regeneration-promoting function of the human gene and/or gene product is conserved.

In those cases where homozygous mutants are viable and fertile, despite the inability to regenerate, they will be bred to produce large numbers of mutant transgenic offspring for pharmacological screening. If homozygous mutants are not viable and/or fertile mutations will be propagated in heterozygotes and heterozygous matings and/or early pressure will be used to produce homozygous mutant transgenic fish for pharmacological screening.

D. Pharmacological Screening

Pharmacological screens are performed on regeneration-deficient fish to define small molecule compounds that promote regeneration of specific cellular populations. Pharmacological screens can be done at low cost and high volume in zebrafish as demonstrated recently (Peterson et al., 2000). Regeneration-deficient fish that are derived from mutagenesis screening have the added advantage of a defined molecular target (the mutated gene) which allows the molecular screen to focus on discrete signaling pathways. In addition, recent advances in combinatorial chemistry (Hulme and Gore, 2003; Mario Geysen et al., 2003; Pinilla et al., 2003) can be brought to bear to define ever more efficacious compounds as lead compounds are reiterated through the process and to increase the efficiency of screening (e.g. utilizing pooled screening of numerous compounds in the first round).

Small molecule compound libraries are obtained from outside sources such as the Chembridge Corporation (San Diego) and prepared as stock solutions in appropriate diluents (e.g. DMSO). For screening, synchronized embryos from matings producing regeneration-deficient fish are arrayed in 96, 24, or 12 well dishes at a defined number of embryos per well appropriate for the size of the well, age of fish screened, and projected percentage of mutants produced. Fish are maintained in embryo medium supplemented with penicillin/ streptomycin (and PTU to block pigmentation if necessary). Fish are subjected to the appropriate ablation protocol for the degenerative condition being modeled. After verification of ablation the prodrug and cytotoxic derivatives are removed by rinsing into new embryo medium several times. Small molecule compounds (or groups of small molecule compounds) are then added to each well and regeneration is assessed over the course of the next few days as described above. If a given molecular compound is expected to be labile in aqueous solution the compound (or group of compounds) could be re-administered.

Compounds which promote cellular regeneration will be further screened to determine the specificity of the effect (e.g. to ensure that the compound is not simply promoting global cell proliferation). Those compounds showing the most promising results can be subjected to combinatorial chemistry modification to create new sub-libraries in an effort to define new compounds with higher efficacy, lower toxicity, better solubility, or any other desirable property. Lead compounds will be investigated further in higher vertebrates with the goal of eventually moving to clinical trials.

There are several distinct advantages of the pro-drug conversion based cellular ablation system when compared to other degeneration model systems: 1) The ablation promoting activity is limited to discrete regions defined by cell and/or tissue subtype expression of the pro-drug converting moiety, thus dramatically reducing complications due to non-specific effects resulting from direct application of cytotoxic agents; 2) Ablation is accomplished quickly in a matter of hours, thus decreasing the time required to perform genetic and pharmacological screens; 3) Pro-drugs are by definition inert prior to conversion, and the specific properties of derived cytotoxic drugs are well described; 4) The disclosed system is highly versatile, in that ablation can be targeted to individual cells or to cellular regions surrounding pro-drug converting competent cells, and finally; 5) The system described is universally applicable, in that it can be applied to any cellular or tissue subtype that can be specified by appropriate DNA regulatory regions. For these reasons the disclosed invention affords significant competitive advantages over other degeneration model systems.

This discovery facilitates inducible ablation of discrete cells, cell types, tissues, or regions and the subsequent detection of any regenerating replacement cells. Also disclosed are methods for using transgenic fish generated with this invention for identifying genetic factors and drug compounds which influence subtype specific cellular regeneration programs. Using this system, cell ablation can be accomplished quickly, reproducibly, and simultaneously in multiple fish, Accordingly, standard mutagenesis approaches can be used to create mutant zebrafish that have a compromised capacity for cellular regeneration. Individual regeneration-deficient mutant fish lines can in turn be used to identify genes necessary for regeneration and, for the discovery of drug compounds capable of promoting cellular regeneration.

Sequence Listing of E. coli K12 Nitroreduetase PCR product:

```
(SEQ ID NO: 3)
5'-atgctcgagccATGGATATCATflCTGTCGCCTTAAAGCGTCATTCC
ACTAAGGCATTTGATGCCAGCAAAAAACTTACCCCGOAACAGGCCGAGCA
GATCAAAACGCTACTGCAATACAGCCCATCCAGCACCAACTCCCAGCCUT
GGCATTFTATTGTTOCCAGCACGGAAGAAGGTAAAGCGCGTGTTGCCAAA
TCCGCTGCCGGTAATTACGTGnCAACGAGCGTAAAATGCTTGATGCCTCc
ICACGTCc3TGGTGrFCTGTGCAAAAACCGCGATGGACGATGTCTGGCTO
AAGCTGGTTGTTGACCAGGAAGATGCCGATGGCCGCTTTGCCACGCCGGA
AGCGAAAOCCGCOAACOATAAAGGTCGCAAGTTCTTCGCTGATATOCACC
UTAAAGATCTGCATGATGATGCAGAOTGGATGGCAAAACAGGTTTATCTC
AACGTCGGTAACTTCCTOCTCGGCGTGGCGGCTCTGGOTCTGGACGCGGT
ACCCATCGAAGGT1TFGACGCCGCCATCCTCGATOCAGAATTTGGTCTGA
AAGAGAAAGGCTACACCAGTCTGGTGGTTGTTCCGGTAGGTCATCACAGC
GTTGAAGAITFTAACGCTACGCTGCCGAAATCTCGTCTGCCGCAAAACAT
CACCTTAACCGAAGTGTAATTCTCTCTTGCCGGGCATCTGCCCGGCTATT
TCCTCTCAGATFCTCCTGATTTGCATAACCCTGTTTCAGCCGTCATCATA
GGCTGCTGTTGTATAAAGGAGACGTTATGCAGGATTTAATATCCCAGGTT
TGAAGAflAGCO0OTAflGAGATCggatcccc-3'.
```

In the sequence listing shown above lower case letters represent sequence added by the primers used for amplification. The nucleotides in capital letters code for the Nitroreduetase gene of E. coli.

REFERENCES

Amsterdam, A., Burgess, S., Golling, G., Chen, W. B., Sun, Z. X., Townsend, K., Farrington, S., Haldi, M., and Hopkins, N. (1999). A large-scale insertional mutagenesis screen in zebrafish, Genes & Development 13, 2713-2724.

Babic, T. (1999). The cholinergic hypothesis of Alzheimer's disease: a review of progress.[comment], Journal of Neurology, Neurosurgery & Psychiatry 67,558.

Bagshawe, K. D., Sharma, S. K., Burke, P. J., Melton, R. G., and Knox, R. J. (1999). Developments with targeted enzymes in cancer therapy, Current Opinion in Immunology 11,579-83.

Beanie, C. E., Raible, D. W., Henion, P. D., and Risen, J. S. (1999). Early pressure screens, Methods in Cell Biology 60,71-86.

Becker, T., Wullimann, M. F., Becker, C. G., Bernhardt, R. R., and Schachner, M. (1997). Axonal regrowth after spinal cord transection in adult zebrafish, Journal of Comparative Neurology 377, 577-595.

Bridgewater, J. A., Knox, R. J., Pius, J. D., Collins, M. K., and Springer, C. 3. (1997). The bystander effect of the nitroreductase/CB 1954 enzyme/prodrug system is due to a cell-permeable metabolite, Human Gene Therapy 8,709-17.

Brockerhoff, S. E., Hurley, J. B., Janssen-Bienhold, U., Neuhauss, S. C., Driever, W., and Dowling, J. E. (1995). A behavioral screen for isolating zebrafish mutants with visual system defects, Proc Nail Acad Sci USA 92, 10545-9.

Burkhardt-Holm, P., Oulini, Y., Schroeder, A., Storch, V., and Braunbeck, T. (1999). Toxicity of 4-ehloroaniline in early life stages of zebrafish (*Danio rerio*): II. Cytopathology and regeneration of liver and gills after prolonged exposure to waterborne 4-chloroaniline, Archives of Environmental Contamination & Toxicology 37, 85-102.

Cameron, D. A., and Carney, L. H. (2000). Cell mosaic patterns in the native and regenerated inner retina of zebrafish: Implications for retinal assembly, Journal of Comparative Neurology 416, 356-367.

Chalfie, M. (1995). Green fluorescent protein, Photochemistry & Photobiology 62, 651-6.

Chalfie, M., Tu, Y., Euskirchen, G., Ward, W. W., and Prasher, D. C. (1994). Green fluorescent protein as a marker for gene expression, Science 263, 802-5.

Chou C Y, Horng L S. Tsai H J (2001) Uniform GFP-expression in transgenic medaka (Oryzias latipes) at the F0 generation. Transgenic Res 10:303-315.

Denny, W. A. (2001). Prodrug strategies in cancer therapy, European Journal of Medicinal Chemistry 36, 577-95.

Denny, W. A. (2002), Nifroreductase-based GDEPT, Current Pharmaceutical Design 8, 1349-61.

Driever, W., Solnica-Krezel, L., Schier, A. F., Neuhauss, S. C., Malieki, L, Stemple, D. L., Stainier, D. Y., Zwartkruis, F., Abdelilah, S., Rangini, Z., et al. (1996). A genetic screen for mutations affecting embryogenesis in zebrafish, Development 123, 37-46.

Driever, W., Stemple, D., Schier, A., and Solnica-Krezel, L. (1994). Zebrafish: genetic tools for studying vertebrate development, Trends in Genetics 10, 152-9.

Fareed, M. U., and Moolten, F. L. (2002). Suicide gene transduction sensitizes murine embryonic and human mesenchymal stem cells to ablation on demand—a fail-safe protection against cellular misbehavior, Gene Therapy 9, 955-962.

Felmer, It, Cui, W., and Clark, A. J. (2002). Inducible ablation of adipocytes in adult transgenic mice expressing the E-coli nitroreductase gene, Journal of Endocrinology 175, 487-498.

Gong, Z., Ju, B., and Wan, H. (2001). Green fluorescent protein (GFP) transgenic fish and their applications, Genetica 111, 213-225.

Grabher C, Henrich T, Sasado T, Arenz A, Wittbrodt J, Furutani-Seiki M (2003) Transposon-mediated enhancer trapping in medaka. Gene 322:57-66.

Gross, L. A., Baird, G. S., Hoffman, R. C., Baldridge, K. K., and Tsien, R. Y. (2000). The structure of the chromophore within DsRed, a red fluorescent protein front coral, Proceedings of the National Academy of Sciences of the United States of America 97, 11990-5.

Grunwald, D. J., and Streisinger, O. (1992). Induction of recessive lethal and specific locus mutations in the zebrafish with ethyl nilrosourea, Genetical Research 59, 103-16.

Haffter, P., Granato, M., Brand, M., Mullins, M. C., Hammerschmidt, M., Kane, D. A., Odenthal, J., van Eeden, F. J., Jiang, Y. J., Heisenberg, C. P., et al. (1996). The identification of genes with unique and essential functions in the development of the zebrafish, *Danio rerio*, Development 123, 1-36.

Hamaoka, T., Takechi, M., Chinen, A., Nishiwaki, Y., and Kawamura, S. (2002). Visualization of rod photoreceptor development using GFP-transgenic zebrafish, Genesis 34, 215-220.

Heim, R., and Tsien, R. Y. (1996). Engineering green fluorescent protein for improved brightness, longer wavelengths and fluorescence resonance energy transfer, Current Biology 6, 178-82.

Henion, P. D., Raible, D. W., Beanie, C. E., Stoesser, K. L., Weston, J. A., and Eisen, J. S. (1996). Screen For Mutations Affecting Development of Zebrafish Neural Crest, Developmental Genetics 18, 11-17.

Houdebine L M, Chourrout D (1991) Transgenesis in fish. Experientia 47:891-897.

Hsiao C D, Hsieh F J, Tsai H J (2001) Enhanced expression and stable transmission of transgenes flanked by inverted terminal repeats from adeno-associated virus in zebrafish. Dev Dyn 220:323-336.

Hulme, C., and Gore, V. (2003). 'Multi-component Reactions Emerging Chemistry in Drug Discovery' From Xylocaln to Crixivan', Current Medicinal Chemistry 10, 51-80.

Ishikawa Y (2000) Medakafish as a model system for vertebrate developmental genetics. Bioessays 22:487-495.

Ismail, R., Millar, V., Cox, V., Davies, B., Doyle, M., Richardson, R., Michael, P., Thomas, N., Briggs, M., F. R., M., and Game, S. M. (2001). Nitroreductase—A New Live Cell Gene Reporter Assay System. Paper presented at: SBS 7th Annual Conference & Exhibition.

Ivics, Z., Izsvak, Z., and Hackett, P. B. (1999). Genetic applications of transposons and other repetitive elements in zebrafish, Methods in Cell Biology 60, 99-131.

Kay, J, N., Roeser, T., Mumm, J. S., Godinho, L., Mrejeru, A. Wong, R. O. L., and Baler, H. (2004). Transient requirement for ganglion cells dining assembly of synaptic layer formation, Development 131, 1331-1342.

Kennedy, B. N., Vihtelic, T. S., Checkley, L., Vaughan, K. T., and Hyde, D. R. (2001). Isolation of a zebrafish rod opsin promoter to generate a transgenic zebrafish line expressing enhanced green fluorescent protein in rod photoreceptors, Journal of Biological Chemistry 276, 14037-14043.

Knox, It J., Boland, M. P., Friedlos, F., Coles, B., Southan, C., and Roberts, J. J. (1988). The nitroreductase enzyme in Walker cells that activates 5-(aziridin-1-yl)-2,4-dinitrobenzamide (CB 1954) to 5-(aziridin-1-yl)-4-hydroxylamino-2-nitrobenzamide is a form of NAD(P)H dehydrogenase (quinone) (EC 1.6.99.2), Biochemical Pharmacology 37, 4671-7.

Koster, R. W., and Fraser, S. B. (2001). Tracing transgene expression in living zebrafish embryos, Developmental Biology 233, 329-346.

Langenau, D. M., Traver, D., Ferrando, A. A., Kutok, J. L., Aster, J. C., Kanki, J. P., Lin, S., Prochownik, E., Trede, N. S., Zon, L. I., and Look, A. T. (2003). Myc-induced T cell leukemia in transgenic zebrafish, Science 299, 887-890.

Lanzky, P. F., and Hailing-Sørensen, B. (1997). The toxic effect of the antibiotic metronidazole on aquatic organisms, Chemosphere 35, 2553-61.

Lauren, D. J., S. J. Teh, et al. (1990). "Cytotoxicity phase of diethylnitrosante-induced hepatic neoplasia in medaka." Cancer Res 50(17):5504-14.

Long, Q., Meng, A., Wang, H., Jessen, J. R., Farrell, M. J., and Lin, S. (1997). GATA-1 expression pattern can be recapitulated in living transgenic zebrafish using GFP reporter gene, Development 124, 4105-11.

Lu J K, Burns J C, Chen T T (1997) Pantropic retroviral vector integration, expression, and germline transmission in medaka (Oryzias latipes). Mol Mar Biol Biotechnol 6:289-295.

Mario Geysen, H., Schoenen, F., Wagner, D., and Wagner, R. (2003). A guide to drug discovery: Combinatorial compound libraries for drug discovery: an ongoing challenge, Nature Reviews Drug Discovery 2, 222-30.

Matsumoto J, Akiyama T, Hirose B, Nakamura M, Yamamoto H, Takeuchi T (1992) Expression and transmission of wild-type pigmentation in the skin of transgenic orange-colored variants of medaka (Oryzias latipes) bearing the gene for mouse tyrosinase. Pigment Cell Res 5:322-327.

Medico, B., Gambarotta, G., Gentile, A., Comoglio, P. M., and Soriano, P. (2001). A gene trap vector system for identifying transcriptionalty responsive genes, Nature Biotechnology 19, 579-582.

Meng, A., Jessen, J. R., and Lin, S. (1999). Transgenesis, Methods in Cell Biology 60, 13348.

Moss, J. B., Price, A. L., Raz, E, Driever, W., and Rosenthal, N. (1996). Green Fluorescent Protein Marks Skeletal Muscle in Murine Cell Lines and Zebrafish, Gene 173, 89-98.

Motoike, T., Loughna, S., Perens, E., Roman, B. L., Liao, W., Chau, T. C., Richardson, C. D., Kawate, T., Kuno, J., Weinstein, B. M., et al. (2000). Universal GFP reporter for the study of vascular development, Genesis 28, 75-81.

Muller F, Blader P. Strable U (2002) Search for enhancers: teleost models in comparative genomic and transgenic analysis of cis regulatory elements. Bioessays 24:564-572.

Mullins, M. C., Hammerschmidt, M., Hafiter, P., and Nusslein-Volhard, C. (1994). Large-scale mutagenesis in the zebrafish: in search of genes controlling development in a vertebrate, Current Biology 4, 189-202.

Mullins, M. C., and Nusslein-Volhard, C. (1993). Mutational approaches to studying embryonic pattern formation in the zebrafish, Current Opinion in Genetics & Development 3, 648-54.

Naciff, J. M., Behbehani, M. M Misawa, H., and Dedman, J. R. (1999). Identification and transgenic analysis of a murine promoter that targets cholinergic neuron expression, Journal of Neurochemistry 72, 17-28.

Naruse K, Fukamachi S, Mitani H, Kondo M, Matsuoka T, Kondo S, Hanamura N, Morita Y, Hasegawa K, Nishigaki R, Shimada A, Wada H, Kusakabe T, Suzuki N, Kinoshita M, Kanamori A, Terado T, Kinmra H, Nonaka M, Shima A (2000) A detailed linkage map of medaka, Oryzias latipes: comparative genomics and genome evolution, Genetics 154: 1773-1784

Nasevicius, A., and Ekker, S. C. (2000). Effective targeted gene 'knockdown' in zebrafish, Nature Genetics 26; 216-220.

Onto K, Kondoh H, Inohara H, Iwamatsu T, Wakamatsu Y, Okada TS (1986) Production of transgenic fish: introduction and expression of chicken delta-crystallin gene in medaka embryos. Cell Differ 19:237-244.

Onto K, Wakamatsu Y, Inoue K (1992) Medaka as a model of transgenic fish. Mol Mar Biol Biotechnol 1:346-354.

Park, H. C., Kim, C. H., Bae, Y. K., Yee, S. Y., Kim, S. H., Hong, S. K., Shin, J., Yoo, K. W., Hibi, M., Hirano, T., et al. (2000). Analysis of upstream elements in the HuC promoter leads to the establishment of transgenic zebrafish with fluorescent neurons, Developmental Biology 227, 279-293.

Patton, E. B., and Zon, L. I. (2001). The art and design of genetic screens: zebrafish, Nature Reviews Genetics 2, 956-66.

Peterson, R. T., Link, B. A., Dowling, J. B., and Schreiber, S. L. (2000). Small molecule developmental screens reveal the logic and timing of vertebrate development, Proceedings of the National Academy of Sciences of the United States of America 97, 12965-9.

Pinilla, C., Appel, J R., Borras, E., and Houghten, R. A. (2003). Advances in the use of synthetic combinatorial chemistry: Mixture-based libraries, Nature Medicine 9, 118-22.

Poss, K. D., Keating, M. T., and Nechiporuk, A. (2003). Tales of regeneration in zebrafish, Development Dynamics 226, 202-210.

Poss, K. D., Wilson, L. G., and Keating, M. T. (2002), Heart regeneration in zebrafish, Science 298, 2188-2190.

Rawls, J. F., Frieda, M. R., McAdow, A. R., Gross, J. P., Clayton, C. M., Heyen, C. K., and Johnson, S. L. (2003). Coupled mutagenesis screen and genetic mapping in zebrafish, Genetics In press.

Reimschussel, R. (2001). A fish model of renal regeneration and development, Ilar Journal 42, 285-91.

Rowlerson, A., Radaefli, G., Mascarello, F., and Veggetti, A. (1997). Regeneration of skeletal muscle in two teleost fish: *Sparus aurata* and *Brachydanio rerio*, Cell & Tissue Research 289, 311-22.

Sato A, Komura J, Masahito P. Matsukuma S, Aoki K, Ishikawa T (1992) Firefly luciferase gene transmission and expression in transgenic medaka (Oryzias latipes), Mol Mar Bid Biotechnol 1:318-325.

Scheer, N., and Campos-Ortega, J. A. (1999). Use of the Gal4-UAS technique for targeted gene expression in the zebrafish, Mechanisms of Development 80, 153-158.

Shinotoh, H., Namba, H., Fukushi, K., Nagatsuka, S., Tanaka, N., Aotsuka, A., Ota, T., Tanada, S., and Irie, T. (2000). Progressive loss of cortical acetylcholinesterase activity in association with cognitive decline in Alzheimer's disease: a positron emission tomography study, Annals of Neurology 48, 194-200.

Solnica-Krezel, L., Sebier, A. F., and Driever, W. (1994). Efficient recovery of ENU-induced mutations from the zebrafish germline, Genetics 136, 1401-20.

Streisinger, G., Walker, C., Dower, N., Knauber, D., and Singer, F. (1981). Production of clones of homozygous diploid zebra fish (*Brachydanio rerio*), Nature 291, 293-6.

Sunderland, T. (1998). Alzheimers disease. Cholinergic therapy and beyond, American Journal of Geriatric Psychiatry 6, S56-63.

Talbot, W. S., and Schier, A. F. (1999). Positional cloning of mutated zebrafish genes, Methods in Cell Biology 60, 259-86.

Tsien, R. Y. (1999). Rosy dawn for fluorescent proteins. [comment], Nature Biotechnology 17, 956-7.

Tsien, R. Y., and Miyawaki, A. (1998). Seeing the machinery of live cells, Science 280, 1954-5.

Vihtelic, T. S., and Hyde, D. R. (2000). Light-induced rod and cone cell death and regeneration the in adult albino zebrafish (Danio rerio) retina, Journal of Neurobiology 44, 289-307.

Wang, X. K., Wan, H. Y., Korzh, V., and Gong, Z. Y. (2000). Use of an IRES bicistronic construct to trace expression of exogenously introduced mRNA in zebrafish embryos, Biotechniques 29.

Wilson, W. R., Pullen, S. M., Hogg, A., Helsby, N. A., Hicks, O., and Denny, W. A. (2002). Quantitation of bystander effects in nitroreductase suicide gene therapy using three-dimensional cell cultures, Cancer Research 62, 1425-1432.

Xu, G., and McLeod, H. L. (2001). Strategies for enzyme/prodrug cancer therapy, Clinical Cancer Research 7, 3314-24.

Zhang, J., Campbell, R. E., Ting, A. Y., and Tsien, R. Y. (2002). Creating new fluorescent probes for cell biology, Nature Reviews Molecular Cell Biology 3, 906-12

Zupanc, G. K. (2001). Adult neurogenesis and neuronal regeneration in the central nervous system of teleost fish, Brain, Behavior & Evolution 58, 250-75.

While the present invention has been described with reference to what are presently considered to be the preferred examples, it is to be understood that the invention is not limited to the examples herein. Rather the scope of the invention is intended to cover various modifications and equivalent arrangements included within the spirit and scope of the appended claims.

What is claimed is:

1. A method for identifying a compound that alters cellular regeneration in a transgenic fish comprising:
   subjecting a transgenic fish to a targeted cellular ablation or a regional cellular ablation, wherein the genome of the transgenic fish comprises a transgene comprising a gene encoding i) an ablation promoting moiety or ii) a coupled expression system comprising an ablation promoting moiety and a reporter protein, wherein the ablation promoting moiety comprises at least one component of a pro-drug conversion system; and wherein the gene is operably-linked to a regulatory DNA sequence comprising at least a promoter element that regulates the expression of the gene such that the gene is expressed in a reproducible spatial and temporal pattern in the transgenic fish;
   contacting the transgenic fish with at least one compound;
   comparing the degree of cellular regeneration in the presence of the compound to a control transgenic fish not contacted with the compound whereby differences in regenerative capacity in the contacted transgenic fish compared to the control transgenic fish indicates that the compound affects cellular regeneration in a transgenic fish; and
   detecting a presence of regenerating cells or an absence of regenerating cells.

2. The method of claim 1, wherein the compound alters cellular regeneration by promoting cellular regeneration.

3. The method of claim 1, wherein the compound alters cellular regeneration by inhibiting cellular regeneration.

4. The method of claim 1, wherein the ablation-promoting moiety comprises a pro-drug converting enzyme.

5. The method of claim 4, wherein the pro-drug converting enzyme comprises a bacterial nitroreductase.

6. The method of claim 1, wherein detecting the presence of regenerating cells comprises a phenotypic change, a remission of a phenotypic change induced by the targeted cellular ablation or the regional cellular ablation, a presence of a reporter protein, and combinations thereof.

7. The method of claim 1, wherein detecting the absence of regenerating cells comprises a phenotypic change, a remission of a phenotypic change induced by the targeted cellular ablation or the regional cellular ablation, an absence of a reporter protein, and combinations thereof.

8. The method of claim 1, wherein the reporter protein is selected from the group consisting of a fluorescent protein, a luminescent protein, and β-galactosidase.

9. The method of claim 1, wherein the transgenic fish is selected from the group consisting of a regeneration-competent transgenic fish and a regeneration-deficient transgenic fish.

10. The method of claim 1, wherein the gene is expressed in a cell selected from the group consisting of a muscle cell, a liver cell, a vascular cell, a neuronal cell, a heart cell, a cartilage cell, and a bone cell.

11. The method of claim 1, wherein the transgenic fish is selected from the group consisting of a transgenic zebrafish and a transgenic medaka.

12. The method of claim 1, wherein the subjecting a transgenic fish to a targeted cellular ablation or a regional cellular ablation comprises subjecting the transgenic fish to a pro-drug.

13. The method of claim 12, wherein the pro-drug is selected from the group consisting of metronidazole, CB1954, and combinations thereof.

14. The method of claim 12, further comprising removal of the pro-drug.

15. The method of claim 12, further comprising removal of a cytotoxic derivative of the pro-drug.

16. The method of claim 1, wherein the transgenic fish comprises a transgenic fish embryo, a transgenic fish larva, and a transgenic fish adult.

17. The method of claim 1, further comprising verifying the targeted cellular ablation or the regional cellular ablation.

18. A method for identifying a compound that alters cellular regeneration in a regeneration-competent transgenic fish comprising:
   subjecting a transgenic fish to a targeted cellular ablation or a regional cellular ablation, wherein the genome of the transgenic fish comprises a transgene comprising a gene encoding i) an ablation promoting moiety or ii) a coupled expression system comprising an ablation promoting moiety and a reporter protein, wherein the ablation promoting moiety comprises at least one component of a pro-drug conversion system; and wherein the gene is operably-linked to a regulatory DNA sequence comprising at least a promoter element that regulates the expression of the gene such that the gene is expressed in a reproducible spatial and temporal pattern in the transgenic fish;
   contacting the transgenic fish with at least one compound;
   comparing the degree of cellular regeneration in the presence of the compound to a control transgenic fish not contacted with the compound whereby differences in regenerative capacity in the contacted transgenic fish compared to the control transgenic fish indicates that the compound affects cellular regeneration in the regeneration-competent transgenic fish; and
   detecting a presence of regenerating cells or an absence of regenerating cells.

19. A method for identifying a compound that alters cellular regeneration in a regeneration-deficient transgenic fish comprising:
   subjecting a transgenic fish to a targeted cellular ablation or a regional cellular ablation, wherein the genome of the transgenic fish comprises a transgene comprising a gene encoding i) an ablation promoting moiety or ii) a coupled expression system comprising an ablation promoting moiety and a reporter protein, wherein the ablation promoting moiety comprises at least one component of a pro-drug conversion system; and wherein the gene is operably-linked to a regulatory DNA sequence comprising at least a promoter element that regulates the expression of the gene such that the gene is expressed in a reproducible spatial and temporal pattern in the transgenic fish;

contacting the transgenic fish with at least one compound;
comparing the degree of cellular regeneration in the presence of the compound to a control transgenic fish not contacted with the compound whereby differences in regenerative capacity in the contacted transgenic fish compared to the control transgenic fish indicates that the compound affects cellular regeneration in the regeneration-deficient transgenic fish; and
detecting a presence of regenerating cells or an absence of regenerating cells.

* * * * *